(12) United States Patent
Cohen et al.

(10) Patent No.: US 10,799,499 B2
(45) Date of Patent: Oct. 13, 2020

(54) COMBINATORIAL THERAPIES OF NEUROLOGICAL DISORDERS

(71) Applicant: PHARNEXT, Issy-les-Moulineaux (FR)

(72) Inventors: Daniel Cohen, Saint-Cloud (FR);
Serguei Nabirotchkin, Chatenay-Malabry (FR); Rodolphe Hajj, Saint-Germain-en-Laye (FR)

(73) Assignee: PHARNEXT, Issy-les-Moulineaux (FR)

( * ) Notice: Subject to any disclaimer, the term of this patent is extended or adjusted under 35 U.S.C. 154(b) by 0 days.

(21) Appl. No.: 16/074,783

(22) PCT Filed: Feb. 3, 2017

(86) PCT No.: PCT/EP2017/052470
§ 371 (c)(1),
(2) Date: Aug. 2, 2018

(87) PCT Pub. No.: WO2017/134280
PCT Pub. Date: Aug. 10, 2017

(65) Prior Publication Data
US 2019/0111054 A1    Apr. 18, 2019

(30) Foreign Application Priority Data

Feb. 5, 2016  (EP) .................................... 16305128
Jan. 23, 2017  (EP) .................................... 17152720

(51) Int. Cl.
| | | |
|---|---|---|
| A61K 31/496 | (2006.01) |
| A61K 31/13 | (2006.01) |
| A61K 31/185 | (2006.01) |
| A61K 31/197 | (2006.01) |
| A61K 31/198 | (2006.01) |
| A61K 31/27 | (2006.01) |
| A61K 31/473 | (2006.01) |
| A61P 25/28 | (2006.01) |
| A61P 25/00 | (2006.01) |
| A61P 25/16 | (2006.01) |
| A61K 31/445 | (2006.01) |
| A61K 31/55 | (2006.01) |

(52) U.S. Cl.
CPC ............ *A61K 31/496* (2013.01); *A61K 31/13* (2013.01); *A61K 31/185* (2013.01); *A61K 31/197* (2013.01); *A61K 31/198* (2013.01); *A61K 31/27* (2013.01); *A61K 31/445* (2013.01); *A61K 31/473* (2013.01); *A61K 31/55* (2013.01); *A61P 25/00* (2018.01); *A61P 25/16* (2018.01); *A61P 25/28* (2018.01)

(58) Field of Classification Search
CPC .... A61K 31/496; A61K 31/473; A61K 31/27; A61K 31/198; A61K 31/197; A61K 31/185; A61K 31/13; A61P 25/16; A61P 25/00; A61P 25/28
See application file for complete search history.

(56) References Cited

U.S. PATENT DOCUMENTS

2014/0371229 A1    12/2014  Cohen et al.

FOREIGN PATENT DOCUMENTS

| EP | 2 796 132 | 10/2014 |
| EP | 2 282 778 | 3/2017 |
| WO | WO 03/080580 | 10/2003 |
| WO | WO 2007/053596 | 5/2007 |
| WO | WO 2008/086492 | 7/2008 |
| WO | WO 2008/087123 | 7/2008 |
| WO | WO 2008/113818 | 9/2008 |
| WO | WO 2009/074607 | 6/2009 |
| WO | WO 2014/037417 | 3/2014 |

OTHER PUBLICATIONS

Codony, X. et al. "5-$HT_6$ receptor and cognition" *Current Opinion in Pharmacology*, Jan. 1, 2011, pp. 94-100, vol. 11, No. 1.
Lanctôt, K. L. et al. "Therapy for Alzheimer's disease: how effective are current treatments?" *Therapeutic Advances in Neurological Disorders*, May 2009, pp. 163-180, vol. 2, No. 3.
Nyholm, D. et al. "Levodopa Infusion Therapy in Parkinson Disease: State of the Art in 2004" *Clinical Neuropharmacology*, Sep.-Oct. 2004, pp. 245-256, vol. 27, No. 5.
Written Opinion in International Application No. PCT/EP2017/052470, dated Jun. 26, 2017, pp. 1-13.

*Primary Examiner* — Sahar Javanmard
(74) *Attorney, Agent, or Firm* — Browdy and Neimark, PLLC

(57) ABSTRACT

The present invention relates to combinations and methods for the treatment of neurological disorders related Amyloid beta toxicity and/or neuronal death. More specifically, the present invention relates to novel combinatorial therapies of Alzheimer's disease, Alzheimer's disease related disorders, Parkinson's disease, Lewy body dementia, multiple system atrophy and other related synucleinopathies, Huntington's disease, peripheral neuropathies, alcoholism or alcohol withdrawal, neurological manifestations of drug abuse or drug abuse withdrawal, amyotrophic lateral sclerosis, multiple sclerosis, spinal cord injury, epilepsy, traumatic brain injury or brain ischemic events based on 3-phenylsulfonyl-8-(piperazin-1-yl) quinoline and baclofen and/or acamprosate.

19 Claims, 2 Drawing Sheets

COMBINATORIAL THERAPIES OF NEUROLOGICAL DISORDERS

CROSS-REFERENCE TO RELATED APPLICATION

This application is the U.S. national stage application of International Patent Application No. PCT/EP2017/052470, filed Feb. 3, 2017.

FIELD OF THE INVENTION

The present invention relates to new combinations and methods for the treatment of neurological diseases and disorders. More specifically, the present invention relates to novel combinatorial therapies of neurological disorders, based on 3-phenylsulfonyl-8-(piperazin-1-yl) quinoline, baclofen and/or acamprosate combinations.

BACKGROUND OF THE INVENTION

Alzheimer's disease (AD) is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (inability to recognize objects, persons, sounds, shapes, or smells) attributable to involvement of the cortical association areas. Special symptoms such as spastic paraparesis (weakness affecting the lower extremities) can also be involved [1-4].

Incidence of AD increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis [5]. United Nations population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources [6].

Memory impairment is the early feature of the disease and involves episodic memory (memory for day-today events). Semantic memory (memory for verbal and visual meanings) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of AD is sufficiently characteristic to allow identification in approximately 80% of cases [7]. Nevertheless, clinical heterogeneity does occur which is important for clinical management but also provides further implication of specific medication treatments for functionally different forms [8].

The pathological hallmark of AD includes amyloid plaques containing beta-amyloid (Abeta), neurofibrillary tangles containing Tau and neuronal and synaptic dysfunction and loss [9-11]. For the last decade, two major hypotheses on the cause of AD have been proposed: the "amyloid cascade hypothesis", which states that the neurodegenerative process is a series of events triggered by the abnormal processing of the Amyloid Precursor Protein (APP) [12], and the "neuronal cytoskeletal degeneration hypothesis" [13], which proposes that cytoskeletal changes are the triggering events. The most widely accepted theory explaining AD progression remains the amyloid cascade hypothesis [14-16] and AD researchers have mainly focused on determining the mechanisms underlying the toxicity associated with Abeta proteins. Microvascular permeability and remodeling, aberrant angiogenesis and blood brain barrier breakdown have been identified as key events contributing to the APP toxicity in the amyloid cascade [17]. On the contrary, Tau protein has received much less attention from the pharmaceutical industry than amyloid, because of both fundamental and practical concerns. Moreover, synaptic density change is the pathological lesion that best correlates with cognitive impairment than the two others. Studies have revealed that the amyloid pathology appears to progress in a neurotransmitter-specific manner where the cholinergic terminals appear most vulnerable, followed by the glutamatergic terminals and finally by the GABAergic terminals [11]. Glutamate is the most abundant excitatory neurotransmitter in the mammalian nervous system. Under pathological conditions, its abnormal accumulation in the synaptic cleft leads to glutamate receptors overactivation [18], that results in pathological processes and finally in neuronal cell death. This process, named excitotoxicity, is commonly observed in neuronal tissues during acute and chronic neurological disorders.

Another principal functional hallmark of AD is profound generalized decline of energy metabolism, in link with oxidative stress [19], and characterized by mitochondrial dysfunction and development of insulin resistance state, leading to reduced glucose uptake and, finally, to synapse collapsing. An impaired brain metabolism is often suggested as a major etiological cause of cognitive decline in age related dementias [20,21] and, in the case of AD, might precede, accompany or even provoke Abeta plaques deposition which, in a vicious circle mechanism, could further inhibit glucose uptake [22].

Up to now, two kinds of medications, accounting for only five drugs approved in most countries, are used for improving or slowing down symptoms of AD which lay on some acetylcholinesterase modulators and a blocker of NMDA glutamate Receptors (NMDAR) [23-25].

Acetylcholinesterase inhibitors such as donepezil, rivastigmine, tacrine and galantamine are currently available in the market and are efficient in symptomatic relief with beneficial effects on cognitive, functional and behavioral symptoms [26].

NMDAR antagonists that target various sites of this receptor have been tested to counteract excitotoxicity. Uncompetitive NMDAR antagonists target the ion channel pore thus reducing the calcium entry into postsynaptic neurons. Only one of them, namely memantine, reached the approval status in moderate to severe AD. This molecule is however of limited benefit in most AD patients, because it has only modest symptomatic effects and further has shown no significant effects in mild Alzheimer's disease [27,28]. Furthermore many other NMDAR antagonists have failed in advanced clinical trials for several neurodegenerative disorders [24,29,30]. Another approach in limiting excitotoxicity consists in inhibiting the presynaptic release of glutamate.

WO2009/133128, WO2009/133141, WO2009/133142, WO2011/054759, and WO2012/117076 disclose drug combinations suitable for use in the treatment of AD. WO2012/117076 particularly discloses the therapeutic efficacy of baclofen-acamprosate combination in AD, including for the protection of glutamate toxicity and/or Abeta toxicity.

3-phenylsulfonyl-8-(piperazin-1-yl) quinoline is a selective 5-HT6 receptor antagonist that has shown some efficacy in treating AD and is currently under clinical trial as an add-on therapy for donepezil. WO2003/080580, WO2005/026125, WO2009/074607 disclose 3-phenylsulfonyl-8-(piperazin-1-yl) quinoline based compositions suitable for use in treating central nervous system diseases.

Despite active research in this area, there is still a need for alternative or improved efficient therapies for neurological disorders and, in particular, neurological disorders which are related to glutamate and/or Abeta toxicity and/or oxidative stress and/or ischemic stress in neuronal cells.

SUMMARY OF INVENTION

The present invention provides new therapeutic methods and compositions suitable for treating neurological disorders, particularly associated with neuronal cell death and cognitive decline. More particularly, the invention relates to compositions comprising 3-phenylsulfonyl-8-(piperazin-1-yl) quinoline in combination with baclofen and/or acamprosate, as well as to the use thereof for treating neurological disorders related to glutamate excitotoxicity and/or amyloid beta (Abeta) toxicity and/or ischemic stress and/or oxidative stress.

The invention stems, inter alia, from the unexpected discovery, by the inventors, that the combination of 3-phenylsulfonyl-8-(piperazin-1-yl) quinoline with baclofen and/or acamprosate particularly strongly protects neuronal cells from various stresses e.g., Abeta toxicity, glutamate toxicity, oxidative stress or ischemic stress, which underlie various neurological disorders.

Thus, combinations of 3-phenylsulfonyl-8-(piperazin-1-yl) quinoline with baclofen and/or acamprosate constitute an efficient treatment for patients suffering from, predisposed to, or suspected to suffer from neurological disorders.

An object of this invention therefore relates to compositions comprising (i) 3-phenylsulfonyl-8-(piperazin-1-yl) quinoline and (ii) baclofen and/or acamprosate.

Another object of this invention relates to compositions comprising 3-phenylsulfonyl-8-(piperazin-1-yl) quinoline in combination with baclofen and/or acamprosate.

A particular object relates to compositions comprising 3-phenylsulfonyl-8-(piperazin-1-yl) quinoline, baclofen and acamprosate.

A further object relates to compositions comprising:
(i) 3-phenylsulfonyl-8-(piperazin-1-yl) quinoline and (ii) baclofen and/or acamprosate, and
a compound selected from donepezil, memantine, rivastigmine, tacrine or galantamine.

As it will be further disclosed in the present application, the compounds in the combinations of the invention may be formulated separately or together. Also, they may be administered simultaneously, separately, sequentially or subsequently to a subject. They can also be administered repeatedly to a subject.

The compositions of the invention typically further comprise one or several pharmaceutically acceptable excipients or carriers. Also, the compounds as used in the present invention may be in the form of a salt, hydrate, ester, ether, acid, amide, racemate, isomer, enantiomerically pure composition or conjugates. They may also be in the form of sustained-release formulations. Prodrugs or derivatives of the compounds may be used as well.

In a preferred embodiment, a compound is used as such or in the form of a salt, hydrate, ester, ether or sustained release form thereof. A particularly preferred salt for use in the present invention is acamprosate calcium.

In another preferred embodiment, a prodrug or derivative is used.

A further object of this invention is a method of preparing a pharmaceutical composition, the method comprising mixing 3-phenylsulfonyl-8-(piperazin-1-yl) quinoline with baclofen and/or acamprosate in a pharmaceutically acceptable excipient or carrier.

Preferably, this method comprises mixing 3-phenylsulfonyl-8-(piperazin-1-yl) quinoline, baclofen and acamprosate in a pharmaceutically acceptable excipient or carrier.

A further object of the invention relates to compositions or combinations as defined above for use in the treatment of a neurological disorder, particularly Alzheimer's disease (AD), an AD related disorder, Parkinson's disease (PD), Lewy body dementia, multiple system atrophy and other related synucleinopathies, Huntington's disease (HD), amyotrophic lateral sclerosis (ALS), multiple sclerosis (MS), peripheral neuropathies, alcoholism or alcohol withdrawal, neurological manifestations of drug abuse or drug abuse withdrawal, spinal cord injury (SCI), epilepsy, traumatic brain injury or a brain ischemic event.

Another object of this invention relates to a method for treating a neurological disorder in a mammalian subject in need thereof, preferably a human subject in need thereof, the method comprising administering to said subject an effective amount of a composition or combination as defined above.

A further object of this invention relates to a method for treating AD or an AD related disorder in a mammalian subject in need thereof, preferably a human subject in need thereof, the method comprising administering to said subject an effective amount of a composition or combination as defined above.

A preferred object of this invention relates to a method for treating a neurological disorder in a mammalian subject in need thereof, preferably a human subject in need thereof, the method comprising simultaneously, separately, sequentially or subsequently administering to said subject an effective amount of 3-phenylsulfonyl-8-(piperazin-1-yl) quinoline, and baclofen and/or acamprosate.

More preferably, this method comprises simultaneously, separately, sequentially or subsequently administering to said subject an effective amount of 3-phenylsulfonyl-8-(piperazin-1-yl) quinoline, baclofen and acamprosate.

A more preferred object of this invention relates to a method for treating AD or an AD related disorder in a mammalian subject in need thereof, preferably a human subject in need thereof, the method comprising simultaneously, separately, sequentially or subsequently administering to said subject an effective amount of 3-phenylsulfonyl-8-(piperazin-1-yl) quinoline, and baclofen and/or acamprosate.

Another preferred object of this invention relates to a method for treating PD or Lewy body dementia, multiple system atrophy and another related synucleinopathy in a mammalian subject in need thereof, preferably a human subject in need thereof, the method comprising simultaneously, separately, sequentially or subsequently administering to said subject an effective amount of 3-phenylsulfonyl-8-(piperazin-1-yl) quinoline, and baclofen and/or acamprosate.

The invention may be used for treating a neurological disorder in any mammalian subject, preferably in any human subject, at any stage of the disease. As it will be disclosed in the examples, the compositions of the invention are able to ameliorate the pathological condition of said subjects.

DETAILED DESCRIPTION OF THE INVENTION

Figure 1:
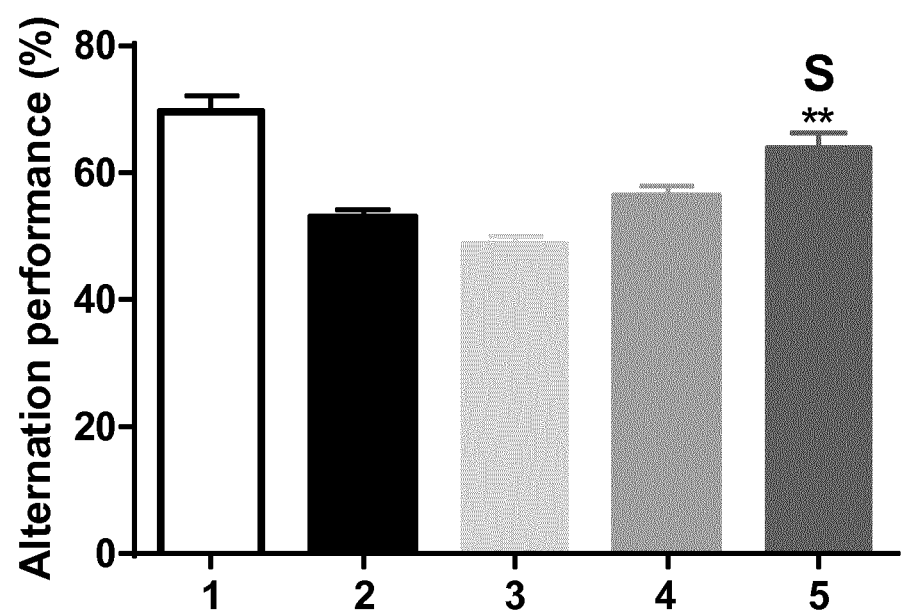
FIGS. 1A-1B: Effect of combination of 3-phenylsulfonyl-8-(piperazin-1-yl) quinoline, baclofen and acamprosate in an in vivo model of cognitive impairment induced by $A\beta_{25-35}$ toxicity. Cognitive impairment was assessed with respect to spatial working memory (Y-maze test—FIG. 1A) and contextual long-term memory (step-through passive avoidance—FIG. 1B). Groups were as follows: (1) Sc.$A\beta_{25-35}$; (2) $A\beta_{25-35}$; (3) $A\beta_{25-35}$/3-phenylsulfonyl-8-(piperazin-1-yl) quinoline (1 mg/Kg); (4) $A\beta_{25-35}$/baclofen and acamprosate (respectively 0.480 mg/Kg and 0.032 mg/Kg); and (5) $A\beta_{25-35}$/3-phenylsulfonyl-8-(piperazin-1-yl) quinoline (1 mg/Kg), baclofen and acamprosate (respectively 0.480 mg/Kg and 0.032 mg/Kg). Data are represented as mean and SEM. Anova followed by a Dunnett's test (vs $A\beta_{25-35}$) (** p-value<0.01). The effect was significantly synergistic (S)(Loewe's test) in both behavioural test (Y-maze CI=0.691 STPA CI=0.996).
Figure 1:
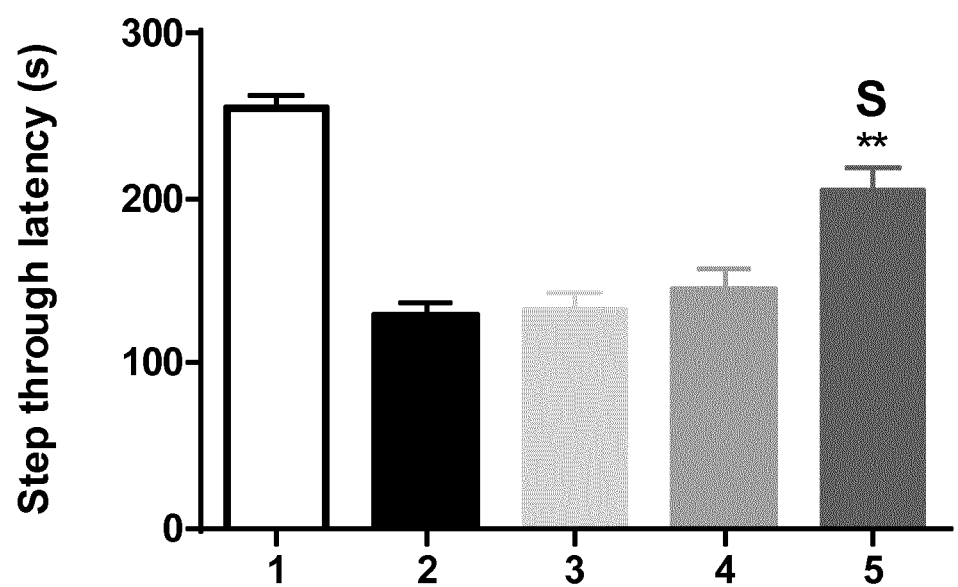

The present invention provides new methods and compositions for treating neurological disorders. The invention discloses novel active compound combinations which allow an effective correction of such diseases and may be used in any mammalian subject.

More particularly, the invention provides novel compositions comprising 3-phenylsulfonyl-8-(piperazin-1-yl) quinoline, baclofen and/or acamprosate. As illustrated in the examples, the presence of 3-phenylsulfonyl-8-(piperazin-1-yl) quinoline surprisingly increases the neuroprotective effect of baclofen or acamprosate or of combinations of baclofen and acamprosate against Abeta oligomer toxicity, glutamate excitotoxicity, oxidative stress induced by 6 OHDA and ischemic stress. The invention is therefore suited for treating any neurological disorders, particularly disorders which involve nerves and/or neurons injuries, beta-amyloid, glutamate excitotoxicity, oxidative stress, ischemic stress and/or cognitive impairment such as neurodegenerative diseases.

An object of the invention therefore resides in a composition or compositions comprising, consisting essentially of or consisting of:
  3-phenylsulfonyl-8-(piperazin-1-yl) quinoline or a pharmaceutically acceptable salt, hydrate, derivative, isomer, racemate, or prodrug thereof, of any chemical purity, and
  baclofen and/or acamprosate, or a pharmaceutically acceptable salt, hydrate, derivative, isomer, racemate, or prodrug thereof, of any chemical purity.

A particular object of the invention resides in a composition or compositions comprising, consisting essentially of or consisting of:
  3-phenylsulfonyl-8-(piperazin-1-yl) quinoline or a pharmaceutically acceptable salt, hydrate, derivative, isomer, racemate, or prodrug thereof, of any chemical purity, and
  baclofen, or a pharmaceutically acceptable salt, hydrate, derivative, isomer, racemate, or prodrug thereof, of any chemical purity, and
  acamprosate, or a pharmaceutically acceptable salt, hydrate, derivative, isomer, racemate, or prodrug thereof, of any chemical purity.

Definitions

"Neurological disorder" refers to diseases including Alzheimer's disease (AD), an AD related disorder, Parkinson's disease (PD), Lewy body dementia, multiple system atrophy and other related synucleinopathies, Huntington's disease (HD), amyotrophic lateral sclerosis (ALS), multiple sclerosis (MS), peripheral neuropathies, alcoholism or alcohol withdrawal, neurological manifestations of drug abuse or drug abuse withdrawal, spinal cord injury (SCI), epilepsy, traumatic brain injury or a brain ischemic event.

"AD related disorder" includes senile dementia of AD type (SDAT), frontotemporal dementia (FTD), vascular dementia, mild cognitive impairment (MCI) and age-associated memory impairment (AAMI).

As used herein, the term "treatment" includes the therapy, prevention, prophylaxis, retardation or reduction of symptoms provoked by or of the causes of the above diseases or disorders. The term treatment includes in particular the control of disease progression and associated symptoms. The term treatment particularly includes a protection against i) the toxicity caused by beta amyloid (Abeta), or a reduction or retardation of said toxicity, and/or ii) a protection against glutamate excitotoxicity, or a reduction or retardation of said toxicity, and/or iii) a protection against 6-OHDA toxicity or a reduction or retardation of said toxicity and/or iv) a protection against ischemic stress or a reduction or retardation of cell mortality under said stress. The term treatment particularly designates an improvement of cognitive symptoms or a protection of neuronal cells.

The term "combination or combinatorial treatment/therapy" designates a treatment wherein 3-phenylsulfonyl-8-(piperazin-1-yl) quinoline and at least baclofen and/or acamprosate are co-administered to a subject to cause a biological effect. In a combined therapy according to this invention, the compounds may be administered together or separately, at the same time, sequentially or subsequently. Also, 3-phenylsulfonyl-8-(piperazin-1-yl) quinoline and baclofen and/or acamprosate may be administered through different routes and protocols.

In a particular embodiment, the combination therapy comprises the simultaneous administration of the compounds, as a single formulation.

In another particular embodiment, the combination therapy comprises the separate administration of 3-phenylsulfonyl-8-(piperazin-1-yl) quinoline, on the one hand, and baclofen and acamprosate, on the other hand.

The combination therapies of the invention also encompass "add-on" therapies, where the subject is already under treatment with some (one or more) of the compounds of a combination of the invention, and the treatment comprises administering the other(s). For instance, in a subject under treatment with 3-phenylsulfonyl-8-(piperazin-1-yl) quinoline, the combination treatment of the invention comprises administering baclofen and/or acamprosate to the subject.

Within the context of this invention, the designation of a specific drug or compound is meant to include not only the specifically named molecule, but also any pharmaceutically acceptable salt, hydrate, derivative, isomer, racemate, enantiomerically pure composition, conjugate, or prodrug thereof, of any chemical purity.

The term "prodrug" as used herein refers to any functional derivatives (or precursors) of a compound of the present invention, which, when administered to a biological system, generates said compound as a result of e.g., spontaneous chemical reaction(s), enzyme catalysed chemical reaction(s), and/or metabolic chemical reaction(s). Prodrugs typically have the structure X-drug wherein X is an inert carrier moiety and drug is the active compound. Usually, the prodrug is devoid of activity or less active than the drug and the drug is released from the carrier in vivo. Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge [31-35]. Furthermore, the preparation of prodrugs may be performed by conventional methods known by those skilled in the art. Methods which can be used to synthesize other prodrugs are described in numerous reviews on the subject [31-38]. For example, arbaclofen placarbil is listed in ChemID plus Advance database (website: chem.sis.nlm nih.gov/chemidplus/) and arbaclofen placarbil is a well-known prodrug of baclofen [39,40].

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, homotaurine is a deacetylated derivative of acamprosate. Preferred derivatives of a compound are molecules having a substantial degree of similarity to said compound, as determined by known methods. Similar compounds along with their index of similarity to a parent molecule can be found in numerous databases such as PubChem (http://pubchem.ncbi.nlm nih-.gov/search/) or DrugB ank (http://www.drugbank.ca/) [41]. In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector [42,43] available online (http://www.ebi.ac.uk/thornton-srv/software/SMSD/). Preferred derivatives should be both structurally and functionally related to a parent compound, i.e., they should also retain at least part of the activity of the parent drug, more preferably they should have a protective activity against Abeta toxicity and/or glutamate toxicity and/or ischemic stress and/or oxidative stress, and or impairment of cognitive function.

The term "derivative" also includes metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug, preferably that has a protective activity against Abeta toxicity and/or glutamate toxicity and/or ischemic stress and/or oxidative stress, and or impairment of cognitive function.

The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartaric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalent, some may have, among others, increased solubility or bioavailability properties. Salt selection is now a common standard operation in the process of drug development as taught by Stahl and Wermuth in their handbook [44].

In a preferred embodiment, the designation of a compound is meant to designate the compound per se, as well as any pharmaceutically acceptable salt, hydrate, isomer, racemate, isomer, enantiomerically pure composition, ester or ether thereof.

In a more preferred embodiment, the designation of a compound is meant to designate the compound as specifically designated per se, as well as any pharmaceutically acceptable salt thereof.

In a particular embodiment, a sustained-release formulation of a compound is used.

Illustrative CAS numbers for baclofen, acamprosate and 3-phenylsulfonyl-8-(piperazin-1-yl) quinoline are provided in Table 1 below. Table 1 cites also, in a non-limitative way, common salts, racemates, isomers, enantiomerically pure compositions, prodrugs, metabolites or derivatives of the compounds according to the invention.

TABLE 1

| Drug | CAS Numbers | Class or Tanimoto similarity index |
|---|---|---|
| Acamprosate and related compounds | | |
| Acamprosate | 77337-76-9; 77337-73-6 | NA |
| Homotaurine | 3687-18-1 | 0.73 |
| Ethyl dimethyl ammonio propane sulfonate | 160255-06-1 | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | NA |

TABLE 1-continued

| Drug | CAS Numbers | Class or Tanimoto similarity index |
|---|---|---|
| 3-(p-chlorophenyl)-4-hydroxybutyric acid | 52977-95-4 | Metabolite |
| Arbaclofen placarbil | 847353-30-4 | Prodrug |
| 3-phenylsulfonyl-8-(piperazin-1-yl) quinolone | | |
| 3-phenylsulfonyl-8-(piperazin-1-yl) quinolone | 607742-69-8; 607742-55-2 | NA |

NA: not applicable

Specific examples of prodrugs of baclofen are given in Hanafi [45], particularly baclofen esters and baclofen ester carbamates, which are of particular interest for central nervous system targeting. Hence such prodrugs are particularly suitable for compositions of this invention. Arbaclofen placarbil as mentioned before is also a well-known prodrug and may thus be used instead of baclofen in compositions of the invention. Other prodrugs of baclofen can be found in the following patent applications: WO2010102071, US2009197958, WO2009096985, WO2009061934, WO2008086492, US2009216037, WO2005066122, US2011021571, WO2003077902 and WO2010120370, that can be used instead of baclofen in the compositions of the invention.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO2009033069, WO2009033061, WO2009033054 WO2009052191, WO2009033079, US 2009/0099253, US 2009/0069419, US 2009/0082464, US 2009/0082440 and US 2009/0076147, that can be used instead of acamprosate in the compositions of the invention.

DESCRIPTION OF THE INVENTION

Preferred combinations of the invention comprise one of the following drug combinations, for combined, separate, sequential or subsequent administration:
  3-phenylsulfonyl-8-(piperazin-1-yl) quinoline and baclofen,
  3-phenylsulfonyl-8-(piperazin-1-yl) quinoline and acamprosate, or
  3-phenylsulfonyl-8-(piperazin-1-yl) quinoline and baclofen and acamprosate.

As discussed above, the drug combinations of the invention have a strong unexpected effect on several biological processes involved in neurological disorders. The inventors have surprisingly discovered that these new compositions can simultaneously, in a synergistic manner, attenuate Abeta toxicity, re-establish disturbed glutamate signaling, attenuate oxidative stress, attenuate ischemic stress in affected neurons, and/or attenuate or reverse impairment of cognitive functions.

The examples show that in a combination therapy of the invention, 3-phenylsulfonyl-8-(piperazin-1-yl) quinoline when combined with baclofen or acamprosate or a combination of baclofen and acamprosate, efficiently protects against Abeta intoxication and/or glutamate excitotoxicity, and/or ischemic stress or 6-OHDA-induced stress, even when compounds are used at lower ranges of concentrations in regard with their protective concentrations when used separately, therefore leading to expect avoiding possible side effects.

In an in vivo model of cognitive impairment, the examples showed that in a combination therapy of the invention, 3-phenylsulfonyl-8-(piperazin-1-yl) quinoline when combined with a combination of baclofen and acamprosate, efficiently and synergistically reversed the impairment of cognitive functions induced by $A\beta(25\text{-}35)$ toxicity.

These drug combinations therefore represent novel approaches for treating neurological disorders, such as AD and AD related disorders, MS, ALS, PD, Lewy body dementia, multiple system atrophy and other related synucleinopathies, HD, peripheral neuropathies, alcoholism or alcohol withdrawal, neurological manifestations of drug abuse or drug abuse withdrawal, SCI, epilepsy, traumatic brain injury or brain ischemic events.

The present invention therefore proposes a novel therapy of neurological disorders, based on combinations of 3-phenylsulfonyl-8-(piperazin-1-yl) quinoline with baclofen and/or acamprosate. More particularly, the present invention proposes a novel therapy of AD and AD related disorders, MS, ALS, PD, Lewy body dementia, multiple system atrophy and other related synucleinopathies, HD, peripheral neuropathies, alcoholism or alcohol withdrawal, neurological manifestations of drug abuse or drug abuse withdrawal, SCI, epilepsy, traumatic brain injury or brain ischemic events, based on combinations of 3-phenylsulfonyl-8-(piperazin-1-yl) quinoline with baclofen and/or acamprosate.

In this regard, in a particular embodiment, the invention relates to a composition comprising 3-phenylsulfonyl-8-(piperazin-1-yl) quinoline with baclofen and/or acamprosate for use in the treatment of AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events.

In a more particular embodiment, the invention relates to one of the following compositions comprising, consisting essentially of or consisting of:
  3-phenylsulfonyl-8-(piperazin-1-yl) quinoline and baclofen,
  3-phenylsulfonyl-8-(piperazin-1-yl) quinoline and acamprosate, or
  3-phenylsulfonyl-8-(piperazin-1-yl) quinoline and baclofen and acamprosate,
for use in the treatment of AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events.

In a further embodiment, the invention relates to one of the following combinations of compounds:
  3-phenylsulfonyl-8-(piperazin-1-yl) quinoline and baclofen,
  3-phenylsulfonyl-8-(piperazin-1-yl) quinoline and acamprosate, or
  3-phenylsulfonyl-8-(piperazin-1-yl) quinoline and baclofen and acamprosate,
for use in the treatment of AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events.

In a combination therapy according to the invention the compounds can be administered separately, simultaneously, sequentially or subsequently to the subject.

In a further embodiment, the invention relates to the use of 3-phenylsulfonyl-8-(piperazin-1-yl) quinoline with baclofen and/or acamprosate for the manufacture of a medicament for the treatment of AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events.

In a particular embodiment, the invention relates to the use of these combinations or compositions for treating AD or an AD related disorder in a subject in need thereof.

In a particular embodiment, the invention relates to the use of these combinations or compositions for treating MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events in a subject in need thereof.

As disclosed in the examples, combination therapies of the invention, comprising at least 3-phenylsulfonyl-8-(piperazin-1-yl) quinoline and baclofen and/or acamprosate show in vitro a very efficient ability to protect neuronal cells from Abeta oligomers toxicity and/or glutamate excitotoxicity and/or 6-OHDA induced oxidative stress and/or ischemic stress. These combinations therefore represent novel approaches for treating neurological disorders, such as AD and AD related disorders, MS, ALS, PD, Lewy body dementia, multiple system atrophy and other related synucleinopathies, HD, peripheral neuropathies, alcoholism or alcohol withdrawal, neurological manifestations of drug abuse or drug abuse withdrawal, SCI, epilepsy, traumatic brain injury or brain ischemic events for treating cognitive symptoms associated with such disorders.

The experimental section further shows that the compositions of the invention are also efficient in synergistically protecting neuronal cells from the above stresses underlying the neurological disorders and improve clinical symptoms such as cognitive impairment in known mice model of cognitive malfunction.

Synergy can be proven through different ways, for instance, by calculating a combinatory index from dose-effect curves of each of the compounds alone and of their combinations [46-48] and/or using the factorial ANOVA test with treatments as factors, indicating whether an interaction between the factors is significant [49]. Synergy may be assessed by methods known by those skilled in the art.

The presented results notably show that the above combination therapies have an important synergistic effect against Abeta toxicity in nervous cells. Such protective synergistic effect is also observed against glutamate toxicity and/or 6-OHDA-induced oxidative stress and/or ischemic stress. These combination therapies represent therefore novel and potent methods for treating AD, AD related disorders but also other disorders which share some these physiological features with AD.

An object of this invention thus also resides in a composition or compositions as defined above for treating a neurological disorder such as AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events.

As mentioned above, the invention is particularly suited for treating AD and AD related disorders, as shown in the experimental section by the results related to Abeta oligomer toxicity and glutamate toxicity, and to a less extend to the results related to less specific stresses as oxidative ischemic stresses. An object of this invention thus also resides in a composition as defined above for treating AD or an AD related disorders further comprising at least one drug selected from are tacrine (CAS: 321-64-2), donepezil (CAS: 120014-06-4), galantamine (CAS: 357-70-0; 1953-04-4), rivastigmine (CAS: 123441-03-2) or memantine (CAS: 19982-08-2).

In a particular embodiment, the invention relates to one of the following compositions per se comprising, consisting essentially of or consisting of:

- 3-phenylsulfonyl-8-(piperazin-1-yl) quinoline and baclofen,
- 3-phenylsulfonyl-8-(piperazin-1-yl) quinoline and acamprosate,
- 3-phenylsulfonyl-8-(piperazin-1-yl) quinoline and baclofen and acamprosate,
- 3-phenylsulfonyl-8-(piperazin-1-yl) quinoline and baclofen and donepezil,
- 3-phenylsulfonyl-8-(piperazin-1-yl) quinoline and acamprosate and donepezil,
- 3-phenylsulfonyl-8-(piperazin-1-yl) quinoline and baclofen and acamprosate and donepezil,
- 3-phenylsulfonyl-8-(piperazin-1-yl) quinoline and baclofen and memantine,
- 3-phenylsulfonyl-8-(piperazin-1-yl) quinoline and acamprosate and memantine,
- 3-phenylsulfonyl-8-(piperazin-1-yl) quinoline and baclofen and acamprosate and memantine,
- 3-phenylsulfonyl-8-(piperazin-1-yl) quinoline and baclofen and acamprosate and tacrine,
- 3-phenylsulfonyl-8-(piperazin-1-yl) quinoline and baclofen and acamprosate and rivastigmine, or
- 3-phenylsulfonyl-8-(piperazin-1-yl) quinoline and baclofen and acamprosate and galantamine.

In a more particular embodiment, the invention relates to one of the following compositions comprising, consisting essentially of or consisting of:

- 3-phenylsulfonyl-8-(piperazin-1-yl) quinoline and baclofen,
- 3-phenylsulfonyl-8-(piperazin-1-yl) quinoline and acamprosate,
- 3-phenylsulfonyl-8-(piperazin-1-yl) quinoline and baclofen and acamprosate,
- 3-phenylsulfonyl-8-(piperazin-1-yl) quinoline and baclofen and donepezil,
- 3-phenylsulfonyl-8-(piperazin-1-yl) quinoline and acamprosate and donepezil,
- 3-phenylsulfonyl-8-(piperazin-1-yl) quinoline and baclofen and acamprosate and donepezil,
- 3-phenylsulfonyl-8-(piperazin-1-yl) quinoline and baclofen and memantine,
- 3-phenylsulfonyl-8-(piperazin-1-yl) quinoline and acamprosate and memantine,
- 3-phenylsulfonyl-8-(piperazin-1-yl) quinoline and baclofen and acamprosate and memantine,
- 3-phenylsulfonyl-8-(piperazin-1-yl) quinoline and baclofen and acamprosate and tacrine,
- 3-phenylsulfonyl-8-(piperazin-1-yl) quinoline and baclofen and acamprosate and rivastigmine, or 3-phenylsulfonyl-8-(piperazin-1-yl) quinoline and baclofen and acamprosate and galantamine for use in the treatment of AD or of an AD related disorder.

In a further embodiment, the invention relates to one of the following combinations of compounds comprising, consisting essentially of or consisting of:
- 3-phenylsulfonyl-8-(piperazin-1-yl) quinoline and baclofen,
- 3-phenylsulfonyl-8-(piperazin-1-yl) quinoline and acamprosate,
- 3-phenylsulfonyl-8-(piperazin-1-yl) quinoline and baclofen and acamprosate,
- 3-phenylsulfonyl-8-(piperazin-1-yl) quinoline and baclofen and donepezil,
- 3-phenylsulfonyl-8-(piperazin-1-yl) quinoline and acamprosate and donepezil,
- 3-phenylsulfonyl-8-(piperazin-1-yl) quinoline and baclofen and acamprosate and donepezil,
- 3-phenylsulfonyl-8-(piperazin-1-yl) quinoline and baclofen and memantine,
- 3-phenylsulfonyl-8-(piperazin-1-yl) quinoline and acamprosate and memantine,
- 3-phenylsulfonyl-8-(piperazin-1-yl) quinoline and baclofen and acamprosate and memantine,
- 3-phenylsulfonyl-8-(piperazin-1-yl) quinoline and baclofen and acamprosate and tacrine,
- 3-phenylsulfonyl-8-(piperazin-1-yl) quinoline and baclofen and acamprosate and rivastigmine, or
- 3-phenylsulfonyl-8-(piperazin-1-yl) quinoline and baclofen and acamprosate and galantamine, for use in the treatment of AD or of an AD related disorders.

The invention is also particularly suited for treating PD, as disclosed in the experimental section by the results related to 6-OHDA toxicity in dopaminergic neurons, glutamate toxicity and ischemic stress. An object of this invention thus also resides in a composition as defined above for treating PD further comprising levodopa or levodopa and carbidopa.

In a particular embodiment, the invention relates to one of the following compositions per se comprising, consisting essentially of or consisting of:
- 3-phenylsulfonyl-8-(piperazin-1-yl) quinoline and baclofen and levodopa
- 3-phenylsulfonyl-8-(piperazin-1-yl) quinoline and acamprosate and levodopa, or
- 3-phenylsulfonyl-8-(piperazin-1-yl) quinoline and baclofen and acamprosate and levodopa.

In a more particular embodiment, the invention relates to one of the following compositions comprising, consisting essentially of or consisting of:
- 3-phenylsulfonyl-8-(piperazin-1-yl) quinoline and baclofen,
- 3-phenylsulfonyl-8-(piperazin-1-yl) quinoline and acamprosate,
- 3-phenylsulfonyl-8-(piperazin-1-yl) quinoline and baclofen and acamprosate, for use in the treatment of PD, Lewy body dementia, multiple system atrophy and other related synucleinopathies.

In an even more particular embodiment, the invention relates to one of the following compositions comprising, consisting essentially of or consisting of:
- 3-phenylsulfonyl-8-(piperazin-1-yl) quinoline and baclofen and levodopa
- 3-phenylsulfonyl-8-(piperazin-1-yl) quinoline and acamprosate and levodopa,
- 3-phenylsulfonyl-8-(piperazin-1-yl) quinoline and baclofen and acamprosate and levodopa, for use in the treatment of PD.

In a further embodiment, the invention relates to one of the following combinations of compounds comprising, consisting essentially of or consisting of:
- 3-phenylsulfonyl-8-(piperazin-1-yl) quinoline and baclofen,
- 3-phenylsulfonyl-8-(piperazin-1-yl) quinoline and acamprosate,
- 3-phenylsulfonyl-8-(piperazin-1-yl) quinoline and baclofen and acamprosate, for use in the treatment of PD, Lewy body dementia, multiple system atrophy and other related synucleinopathies.

In another embodiment, the invention relates to one of the following combinations of compounds comprising, consisting essentially of or consisting of:
- 3-phenylsulfonyl-8-(piperazin-1-yl) quinoline and baclofen and levodopa
- 3-phenylsulfonyl-8-(piperazin-1-yl) quinoline and acamprosate and levodopa,
- 3-phenylsulfonyl-8-(piperazin-1-yl) quinoline and baclofen and acamprosate and levodopa, for use in the treatment of PD.

As indicated previously, in a combination therapy of this invention, the compounds or drugs may be formulated together or separately, and administered together, separately, sequentially or subsequently.

A further object of this invention resides in the use of a composition or a combination as defined above for the manufacture of a medicament for treating a neurological disorder such as AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events.

The invention further provides a method for treating a neurological disorder such as AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events comprising administering to a subject in need thereof an effective amount of a composition or combination as disclosed above.

A further object of the invention is a method of treating a neurological disorder such as AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events, the method comprising simultaneously, separately, sequentially or subsequently administering to a subject in need thereof an effective amount of a combination as disclosed above.

A further object of the invention is a method of treating a neurological disorder such as AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events, the method comprising subsequently administering to a subject in need thereof and already treated with 3-phenylsulfonyl-8-(piperazin-1-yl) quinoline, an effective amount of baclofen and/or acamprosate. A further object of the invention is a method of treating a neurological disorder such as AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events, the method comprising subsequently administering to a subject in need thereof and already treated with baclofen and/or acamprosate [derivative], an effective amount of 3-phenylsulfonyl-8-(piperazin-1-yl) quinoline.

In a preferred embodiment, the invention relates to a method of treating a neurological disorder such as AD, AD related disorders, MS, PD, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events, in a subject in need thereof, comprising administering simultaneously, separately, sequentially or subsequently to the subject an effective amount of 3-phenylsulfonyl-8-(piperazin-1-yl) quinoline and baclofen and/or acamprosate.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds in an appropriate excipient or carrier.

In a particular embodiment, the method comprises mixing 3-phenylsulfonyl-8-(piperazin-1-yl) quinoline, baclofen and acamprosate in an appropriate excipient or carrier.

According to preferred embodiments of the invention, as indicated above, the compounds are used as such or in the form of a pharmaceutically acceptable salt, prodrug, derivative, or sustained/controlled release formulation thereof.

Although very effective in vivo, depending on the subject or specific condition, the combination therapy of the invention may further be used in conjunction or association or combination with additional drugs or treatments beneficial to treating neurological condition in the subjects.

Other therapies used in conjunction with drug(s) or drug(s) combination(s) according to the present invention, may comprise one or more drug(s) that ameliorate symptoms of MS, Lewy body dementia, multiple system atrophy and other related synucleinopathies, ALS, HD, peripheral neuropathies, alcoholism or alcohol withdrawal, neurological manifestations of drug abuse or drug abuse withdrawal, SCI, epilepsy, traumatic brain injury or brain ischemic events, or drug(s) that could be used for palliative treatment of these disorders. Thereby, illustrative therapies which can be used with combinations of the invention are tacrine (CAS: 321-64-2), donepezil (CAS: 120014-06-4), galantamine (CAS: 357-70-0; 1953-04-4), rivastigmine (CAS: 123441-03-2) or memantine (CAS: 19982-08-2) for AD and AD related disorders, or lisuride (CAS: 140387-89-9, 1189731-50-7, 14611-52-0, 14611-51-9), rasagiline (CAS: 136236-51-6), tolcapone (CAS: 134308-13-7), entacapone (CAS: 130929-57-6), clozapine (CAS: 5786-21-0), desipramine (CAS: 50-47-5), citalopram (CAS: 59729-33-8), nortriptyline (CAS: 72-69-5), paroxetine (CAS: 61869-08-7), atomoxetine (CAS: 82248-59-7), venlafaxine (CAS: 93413-69-5), amantadine (CAS: 768-94-5), donepezil (CAS: 120014-06-4), rivastigmine (CAS: 123441-03-2), memantine (CAS: 19982-08-2), bromocriptine (CAS: 25614-03-3), cabergoline (CAS: 81409-90-7), pergolide (CAS: 66104-22-1), pramipexole (CAS: 104632-26-0), ropinirole (CAS: 91374-21-9), rotigotine (CAS: 99755-59-6, 92206-54-7), apomorphine (CAS: 58-00-4), carbidopa (CAS: 28860-95-9), benserazide (CAS: 322-35-0), selegiline (CAS: 14611-51-9), omigapil (CAS: 181296-84-4), CEP-1347 (CAS: 156177-65-0), isradipine (CAS: 75695-93-1) or DOPA (CAS: 59-92-7) for PD, or lithium or riluzole (CAS: 1744-22-5) for ALS, or levetiracetam (CAS: 102767-28-2), ezogabine (CAS: 150812-12-7), pregabalin (CAS: 148553-50-8), rufinamide (CAS: 106308-44-5), felbamate (CAS: 25451-15-4), carbamazepine (CAS: 298-46-4), valproate (CAS: 99-66-1), sodium valproate (CAS: 1069-66-5), lamotrigine (CAS: 84057-84-1), phenytoin (CAS: 57-41-0), oxcarbazepine (CAS: 28721-07-5), ethosuximide (CAS: 77-67-8, 39122-19-5, 39122-20-8), gabapentin (CAS: 60142-96-3), tiagabine (CAS: 115103-54-3), topiramate (CAS: 97240-79-4), vigabatrin (CAS: 60643-86-9), phenobarbital (CAS: 50-06-6), primidone (CAS: 125-33-7) and clonazepam (CAS: 1622-61-3) for epilepsy, or interferon beta-1a (CAS: 145258-61-3), interferon beta-1b (CAS: 145155-23-3), mitoxantrone (CAS: 65271-80-9), natalizumab (CAS: 189261-10-7), fingolimod (CAS: 162359-55-9), natalizumab (CAS: 189261-10-7), teriflunomide (CAS: 108605-62-5), dimethyl fumarate (CAS: 624-49-7, 23057-98-9) or glatiramer (CAS: 28704-27-0; 147245-92-9) for MS.

Therapy according to the invention may be provided at home, the doctors office, a clinic, a hospital's outpatient department, or a hospital, so that the doctor can observe the therapy's effects closely and make any adjustments that are needed.

The duration of the therapy depends on the stage of the disease being treated, age and condition of the patient, and how the patient responds to the treatment. The dosage, frequency and mode of administration of each component of the combination can be controlled independently. For example, one compound may be administered orally while the second compound may be administered intramuscularly. Combination therapy may be given in on-and-off cycles that include rest periods so that the patient's body has a chance to recovery from any as yet unforeseen side-effects. The compounds may also be formulated together such that one administration delivers all drugs.

The administration of each compound of the combination may be by any suitable means that results in a concentration of the compound that, combined with the other component(s), is able to ameliorate the patient condition and/or efficiently treat the disease or disorder.

While it is possible for the compounds of the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable and adapted for use for treatment with the combinations of the present invention.

The compound(s) may be contained, in any appropriate amount, in any suitable carrier substance. The compound(s) may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy [50] and the Encyclopedia of Pharmaceutical Technology [51]).

Pharmaceutical compositions according to the invention may be formulated to release the active compound(s) substantially immediately upon administration or at any predetermined time or time period after administration.

The sustained/controlled release formulations include (i) formulations that create a substantially constant concentration of the compound within the body over an extended period of time; (ii) formulations that after a predetermined lag time create a substantially constant concentration of the compound within the body over an extended period of time; (iii) formulations that sustain compound action during a predetermined time period by maintaining a relatively, constant, effective drug level in the body with concomitant minimization of undesirable side effects associated with fluctuations in the plasma level of the active drug substance; (iv) formulations that localize compound action by, e.g., spatial placement of a controlled release composition adjacent to or in the diseased tissue or organ; and (v) formulations that target compound action by using carriers or chemical derivatives to deliver the drug to a particular target cell type.

Administration of drugs in the form of a sustained/controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain sustained/controlled release in which the rate of release outweighs the rate of metabolism of the compound in question. Controlled release may be obtained by appropriate selection of various formulation parameters and ingredients, including, e.g., various types of controlled release compositions and coatings. Thus, the compound is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active compound substance in a predetermined pattern (e.g., in order to achieve a controlled release formulation) or it may be adapted not to release the active compound substance until after passage of the stomach (enteric coating). The coating may be a sugar coating, a film coating (e.g., based on hydroxypropyl methylcellulose, methylcellulose, methyl hydroxyethylcellulo se, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology [51].

Drugs/compounds may be mixed together in the tablet, or may be partitioned. For example, a first compound is contained on the inside of the tablet, and a second compound is on the outside, such that a substantial portion of the second compound is released prior to the release of the first compound.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders, granulates, micro- or nano-particles may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition(s) may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active compound(s), the composition may include suitable parenterally acceptable carriers and/or excipients. The active compound(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active compound(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compound(s) is/are only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active compound(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamnine) Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active compound(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Slow Release Formulations

Any of the compounds of the combinatorial therapy of the invention may be used in slow release formulations, and/or formulated with agents that modify tissue distribution or bioavailability. More particularly, when applicable, one or more compound(s) of the therapy of the invention are formulated with drug eluting polymer or biomolecules or micelles or liposome-forming lipids or oil in water emulsions, or pegylated or solid nanoparticles or microparticles for oral or parenteral or intrathecal administration to modify tissue distribution or bioavailability. Specific examples of such formulating agents include PGA, PLGA, cyclodextrins, albumin or protein carriers, nano and microparticles, liposomes, emulsions, and PEG.

Conjugates

In combination therapies of this invention, the compounds may be associated in pharmaceutical compositions in different ways. They may be mixed together as separate entities. They may be formulated separately. They may also be linked, covalently or non-covalently, with or without a linker. In a particular embodiment, at least two compounds are linked, preferably through a cleavable or non-cleavable linker.

Dosages and Duration of the Treatment

It will be appreciated that the drugs/compounds of the combination(s) may be administered concomitantly, either in the same or different pharmaceutical formulation, sequentially or subsequently. If there is sequential or subsequent administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the compounds in a combination of this invention include, e.g., amounts that are effective for reducing AD symptoms, halting or slowing the progression of the disease once it has become clinically manifest, or prevention or reduction of the risk of developing the disease.

The active drugs of the present invention may be administered in divided doses, for example two or three times daily. Moreover, different frequency of administration may be used for each compound, e.g., one compound may be administered once daily whereas the other compounds may be administered twice daily. A single administration of a composition of 3-phenylsulfonyl-8-(piperazin-1-yl) quinoline per day, associated with a twice daily administration of a composition of baclofen and acamprosate is preferred. As an alternative embodiment, a single daily dose of each compound in the combination is preferred, with a single daily dose of all drugs in a single pharmaceutical composition (unit dosage form) being most preferred.

Administration can be repeated for several days to several years, and may even be for the life of the patient. Chronic or at least periodically repeated long-term administration is indicated in most cases.

Likewise, administration can also be once every two days, three to two days per week or once weekly. There also, different frequency of administration may be used for each compound.

The term "unit dosage form" refers to physically discrete units (such as capsules, tablets, loaded syringe cylinders, shaker cups, ampoule) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually low or no effect. Accordingly, a particular advantage of the invention lies in the ability to use suboptimal doses of each compound, i.e., doses which are lower than therapeutic doses usually prescribed, preferably ½ of therapeutic doses, more preferably ⅓, ¼, ⅕, ⅙, ⅐, ⅛, ⅑ or even more preferably ¹⁄₁₀ of therapeutic doses. In particular examples, doses as low as ¹⁄₂₀, ¹⁄₃₀, ¹⁄₅₀, ¹⁄₁₀₀, or even lower, of therapeutic doses are used.

At such sub-therapeutic dosages, the compounds would exhibit lower to no side effect, while the combination(s) according to the invention are fully effective in treating neurological disorders.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Also, when therapies of the invention also comprise administering donepezil, memantine, rivastigmine, tacrine, or galantamine or levodopa, these drugs are used either at their usual dose and regimen (i.e. as an add-on therapy) or even at a lower dose, from 1% up to 50% of those usually prescribed in their respective indications.

Specific examples of dosages of compounds for use in the invention are provided below:

acamprosate between 0.01 µg and 1000 mg/day, preferably less than 400 mg/day, preferably less than 200 mg/day, more preferably less than 100 mg/day, even more preferably less than 50 mg/day, preferably less than 1 mg/day, preferably less than 0.5 mg/day, preferably less than 10 µg/day, more preferably less than 1 µg/day, even more preferably less than 0.1 µg/day such dosages being particularly suitable for oral administration.

baclofen between 0.0001 µg/day and 150 mg/day, preferably less than 100 mg/day, more preferably less than 50 mg/day, even more preferably less than 25 mg/day, preferably less than 1 mg/day, preferably less than 0.5 mg/day, preferably less than 10 µg/day, preferably less than 1 µg/day, preferably less than 0.1 µg/day, more preferably less than 0.01 µg/day, even more preferably less than 0.001 µg/day such dosages being particularly suitable for oral administration.

3-phenylsulfonyl-8-(piperazin-1-yl) quinoline between 0.5 and 75 mg/day, preferably less than 35 mg/day, preferably less than 17 mg/day, more preferably less than 5 mg/day, even more preferably less than 1 mg/day, such dosages being particularly suitable for oral administration.

donepezil between 0.5 and 23 mg/day, preferably less than 10 mg/day, more preferably less than 5 mg/day even more preferably less than 2 mg/day, such dosages being particularly suitable for oral administration.

memantine between 0.5 and 20 mg/day, preferably less than 10 mg/day, more preferably less than 5 mg/day even more preferably less than 2 mg/day, such dosages being particularly suitable for oral administration.

tacrine between 0.4 and 160 mg/day, preferably less than 80 mg/day, more preferably less than 40 mg/day, even more preferably less than 20 mg/day, such dosages being particularly suitable for oral administration.

rivastigmine between 0.3 and 12 mg/day, preferably less than 6 mg, more preferably less than 3 mg/day.

galantamine between 0.8 and 24 mg/day, preferably less than 12 mg, more preferably less than 6 mg/day even more preferably 3 mg/day.

levodopa between 0.1 and 6 g per day, preferably less than 3 g per day, more preferably less than 1 g per day, even more preferably less than 500 mg per day.

Pharmaceutical compositions can be formulated to provide per oral dose between:

acamprosate between 0.01 µg and 1000 mg, preferably less than 400 mg, preferably less than 200 mg, more preferably less than 100 mg, even more preferably less than 50 mg, preferably less than 1 mg, preferably less than 0.5 mg, preferably less than 10 µg, more preferably less than 1 µg, even more preferably less than 0.1 µg such dosages being particularly suitable for oral administration;

baclofen between 0.0001 µg and 150 mg, preferably less than 100 mg, more preferably less than 50 mg, even more preferably less than 25 mg, preferably less than 1 mg, preferably less than 0.5 mg, preferably less than 10 µg, preferably less than 1 µg, preferably less than 0.1 µg, more preferably less than 0.01 µg, even more preferably less than 0.001 µg such dosages being particularly suitable for oral administration;

3-phenylsulfonyl-8-(piperazin-1-yl) quinoline between 0.5 and 75 mg, preferably less than 35 mg, preferably less than 17 mg, more preferably less than 5 mg, even more preferably less than 1 mg, such dosages being particularly suitable for oral administration;

donepezil between 0.5 and 23 mg, preferably less than 10 mg, more preferably less than 5 mg even more preferably less than 2 mg, such dosages being particularly suitable for oral administration;

memantine between 0.5 and 20 mg, preferably less than 10 mg, more preferably less than 5 mg even more preferably less than 2 mg, such dosages being particularly suitable for oral administration;

tacrine between 0.4 and 160 mg, preferably less than 80 mg, more preferably less than 40 mg, even more preferably less than 20 mg, such dosages being particularly suitable for oral administration;

rivastigmine between 0.3 and 12 mg, preferably less than 6 mg, more preferably less than 3 mg;

galantamine between 0.8 and 24 mg, preferably less than 12 mg, more preferably less than 6 mg even more preferably 3 mg, and/or levodopa between 0.1 and 6 g, preferably less than 3 g, more preferably less than 1 g, even more preferably less than 500 mg.

Moreover, pharmaceutical compositions of the invention can be formulated to comprise, as active ingredient:

acamprosate in an amount from between 0.001 µg to 16 mg/kg of human subject, preferably less than 7 mg/kg of human subject, preferably less than 4 mg/kg of human subject, more preferably less than 2 mg/kg of human subject, even more preferably less than 1 mg/kg of human subject, preferably less than 0.2 mg/kg of human subject, preferably less than 0.1 mg/kg of human subject, preferably less than 0.2 µg/kg of human subject, more preferably less than 0.02 µg/kg of human subject y, even more preferably less than 0.002 µg/kg of human subject such dosages being particularly suitable for oral administration;

baclofen in an amount from between 0.000002 µg and 3 mg/kg of human subject, preferably less than 2 mg/kg of human subject, more preferably less than 1 mg/kg of human subject, even more preferably less than 0.5 mg/kg of human subject, preferably less than 0.02 mg/kg of human subject, preferably less than 0.01 mg/kg of human subject, preferably less than 0.2 µg/kg of human subject, preferably less than 0.02 µg/kg of human subject, preferably less than 0.002 µg/kg of human subject, more preferably less than 0.0002 µg/kg of human subject, even more preferably less than 0.00002 µg/kg of human subject such dosages being particularly suitable for oral administration;

3-phenylsulfonyl-8-(piperazin-1-yl) quinoline in an amount from between 0.01 to 1.25 mg/kg of human subject, preferably less than 0.6 mg/kg of human subject, preferably less than 0.3 mg/kg of human subject, more preferably less than 0.1 mg/kg of human subject, even more preferably less than 0.02 mg/kg of human subject, such dosages being particularly suitable for oral administration;

donepezil in an amount from between 0.01 to 0.4 mg/kg of human subject, preferably less than 0.2 mg/kg of human subject, more preferably less than 0.1 mg/kg of human subject even more preferably less than 0.04 mg/kg of human subject, such dosages being particularly suitable for oral administration;

memantine in an amount from between 0.01 and 0.4 mg/kg of human subject, preferably less than 0.2 mg/kg of human subject, more preferably less than 0.1 mg/kg of human subject even more preferably less than 0.04 mg/kg of human subject, such dosages being particularly suitable for oral administration;

tacrine in an amount from between 0.006 to 2.7 mg/kg of human subject, preferably less than 1.3 mg/kg of human subject, more preferably less than 0.7 mg/kg of human subject, even more preferably less than 0.4 mg/kg of human subject, such dosages being particularly suitable for oral administration;

rivastigmine in an amount between 0.005 to 0.2 mg/kg of human subject, preferably less than 0.1 mg kg of human subject, more preferably less than 0.005 mg/kg of human subject;

galantamine in an amount between 0.013 to 0.4 mg/kg of human subject, preferably less than 0.2 mg/kg of human subject, more preferably less than 0.1 mg/kg of human subject even more preferably 0.05 mg/kg of human subject; and/or levodopa in an amount between 0.016 to 0.1 g/kg of human subject, preferably less than 0.5 g/kg of human subject, more preferably less than 0.017 g/kg of human subject, even more preferably less than 10 mg/kg of human subject.

In the compositions of the invention, baclofen and acamprosate may be used in different ratios, e.g., at a weight ratio acamprosate/baclofen comprised between 0.05 and 1000 (w/w), preferably between 0.05 and 100 (w/w), more preferably between 0.05 and 50 (w/w).

It will be understood that the amount of the compounds actually administered will be determined by a physician, in the light of the relevant circumstances including the condition or conditions to be treated, the exact composition to be administered, the age, weight, and response of the patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

A—Combination Therapies of the Invention Prevent Toxicity of Human $A\beta_{1-42}$ In Vitro Effect on the Toxicity of Human Aβ1-42 Peptide on Primary Cortical Neuron Cells.

Culture of Primary Cortical Neurons

Rat cortical neurons are cultured as described by Singer et al. [52]. Briefly pregnant female rats of 15 days gestation were killed by cervical dislocation (Rats Wistar) and the foetuses were removed from the uterus. The cortex was removed and placed in ice-cold medium of Leibovitz (L15) containing 2% of Penicillin 10.000 U/ml and Streptomycin 10 mg/ml and 1% of bovine serum albumin (BSA). Cortices were dissociated by trypsin for 20 min at 37° C. (0.05%). The reaction was stopped by the addition of Dulbecco's modified Eagle's medium (DMEM) containing DNase 1 grade II and 10% of fetal calf serum (FCS). Cells were then mechanically dissociated by 3 serial passages through a 10 ml pipette and centrifuged at 515×g for 10 mM at +4° C. The supernatant was discarded and the pellet of cells was re-suspended in a defined culture medium consisting of Neurobasal supplemented with B27 (2%), L-glutamine (0.2 mM), 2% of PS solution and 10 ng/ml of BDNF. Viable cells are counted in a Neubauer cytometer using the trypan blue exclusion test. The cells are seeded at a density of 30 000 cells/well in 96 well-plates (wells were pre-coated with poly-L-lysine (10 μg/ml)) and are cultured at +37° C. in a humidified air (95%)/CO2 (5%) atmosphere.

Three independent cultures are performed per condition, 6 wells per condition.

Test compounds and Human Amyloid-β1-42 Treatment

Briefly, $A\beta_{1-42}$ peptide is reconstituted in define culture medium at 40 μM (mother solution) and was slowly shaken at +37° C. for 3 days in dark. The control medium is prepared in the same conditions.

After 3 days, the solution is used on primary cortical neurons as follows.

After 10 days of neuron culture, test compounds and combinations thereof are solved in culture medium (+0.1% DMSO) and then pre-incubated with neurons for one hour before the $A\beta_{1-42}$ application (in a final volume per culture well of 100 μl). One hour after test compound(s) incubation, 100 μl of $A\beta_{1-42}$ peptide is added to a final concentration of 10 μM diluted in presence of drug(s), in order to avoid further test compound(s) dilutions. Cortical neurons are intoxicated for 24 h. Three separate cultures are performed per condition, 6 wells per condition.

BDNF (50 ng/ml) is used as positive control. Three separate cultures are performed per condition, 12 wells per condition.

MAP2 Antibody Labelling Assay 24 hours after intoxication, the cell culture supernatant is taken off and the cortical neurons are fixed by a cold solution of ethanol (95%) and acetic acid (5%) for 5 min at −20° C. After permeabilization with 0.1% of saponin, cells are incubated for 2 h with mouse monoclonal antibody anti microtubule-associated-protein 2 (MAP-2; Sigma) at dilution of 1/400 in PBS containing 1% fetal calf serum and 0.1% of saponin (this antibody stains specifically cell bodies and neurites, allowing study of both the neurite network and cell death). This antibody is revealed with Alexa Fluor 488 goat anti-mouse IgG (Molecular probe) at the dilution of 1/400 in PBS containing 1% fetal calf serum and 0.1% of saponin for 1 H at room temperature. For each condition, 30 pictures per well are taken using InCell Analyzer™ 1000 (GE Healthcare) with 20× magnification. All images are taken with the same conditions. Analysis of total neurite network and number of neurons is performed automatically by using Developer software (GE Healthcare).

Data Processing

Data are expressed in percentage of control conditions (no intoxication, no amyloid=100%) in order to express the amyloid injury. All values are expressed as mean+/−SEM (s.e.mean) of the 3 cultures (n=6 wells per condition). Statistical analyses are done on the different conditions (one-way ANOVA followed by the Dunnett's test when it is allowed, Statview software version 5.0).

Results'

Results show that tested combinations are efficient in protecting neuronal cells against $A\beta_{1-42}$ toxicity (Table 2). Of note, these combinations show an effective protective effect on neuronal cells at doses where 3-phenylsulfonyl-8-(piperazin-1-yl) quinoline, baclofen, acamprosate, rivastigmine, galantamine, tacrine, memantine or donepezil when used alone show no or a marginal protective effect.

TABLE 2

| Drug combination | Protective activity against Aβ toxicity in nervous cells |
|---|---|
| 3-phenylsulfonyl-8-(piperazin-1-yl) quinolone and baclofen | + |
| 3-phenylsulfonyl-8-(piperazin-1-yl) quinolone and acamprosate | + |
| 3-phenylsulfonyl-8-(piperazin-1-yl) quinolone and baclofen and acamprosate | + |
| 3-phenylsulfonyl-8-(piperazin-1-yl) quinolone and baclofen and donepezil | + |
| 3-phenylsulfonyl-8-(piperazin-1-yl) quinolone and acamprosate and donepezil | + |
| 3-phenylsulfonyl-8-(piperazin-1-yl) quinolone and baclofen and acamprosate and donepezil | + |
| 3-phenylsulfonyl-8-(piperazin-1-yl) quinolone and baclofen and memantine | + |

TABLE 2-continued

| Drug combination | Protective activity against Aβ toxicity in nervous cells |
|---|---|
| 3-phenylsulfonyl-8-(piperazin-1-yl) quinolone and acamprosate and memantine | + |
| 3-phenylsulfonyl-8-(piperazin-1-yl) quinolone and baclofen and acamprosate and memantine | + |
| 3-phenylsulfonyl-8-(piperazin-1-yl) quinolone and baclofen and acamprosate and tacrine | + |
| 3-phenylsulfonyl-8-(piperazin-1-yl) quinolone and baclofen and acamprosate and rivastigmine | + |
| 3-phenylsulfonyl-8-(piperazin-1-yl) quinolone and baclofen and acamprosate and galantamine | + |

B—Prevention of Glutamate Toxicity on Neuronal Cells

Glutamate toxicity is involved in the pathogenesis of numerous neurological diseases or disorders such as multiple sclerosis, Alzheimer's Disease, AD related disorders, amyotrophic lateral sclerosis, Parkinson's Disease, Lewy body dementia, multiple system atrophy or PD related synucleinopathies, Huntington's Disease, neuropathies, alcoholism or alcohol withdrawal, neurological manifestation of drug abuse or drug abuse withdrawal, epilepsy, traumatic brain injury or a brain ischemic event or spinal cord injury. The drugs are first tested individually, followed by assays for their combinatorial action. In this set of experiments, compounds have been tested for their ability to prevent or reduce the toxic effects of glutamate on neuronal cells.

Neuronal Cell Preparation

The Efficacy of Drug Combinations of the Invention is Assessed on Primary Cortical Neuron cells.

Cells are prepared as previously.

Glutamate Toxicity Assays

The neuroprotective effect of compounds is assessed by quantification of the neurite network (Neurofilament immunostaining (NF)) which specifically reveals the glutamatergic neurons.

After 12 days of neuron culture, drugs of the candidate combinations are solved in culture medium (+0.1% DMSO). Candidate combinations and drugs are then pre-incubated with neurons for 1 hour before the glutamate injury. One hour after incubation with, glutamate is added for 20 min, to a final concentration of 40 μM, in presence of candidate combinations, in order to avoid further drug dilutions. At the end of the incubation, medium is changed with medium with candidate combination but without glutamate. The culture is fixed 24 hours after glutamate injury. MK801 (dizocilpine-hydrogen maleate, 77086-22-7-20 μM) is used as a positive control.

After permeabilization with saponin (Sigma), cells are blocked for 2 h with PBS containing 10% goat serum, then the cells are incubated with mouse monoclonal primary antibody against Neurofilament antibody (NF, Sigma). This antibody is revealed with Alexa Fluor 488 goat anti-mouse IgG.

Nuclei of cells are labeled by a fluorescent marker (Hoechst solution, SIGMA), and neurite network quantified. Six wells per condition are used to assess neuronal survival in 3 different cultures.

Results

All of the tested drug combinations give a protective effect against glutamate toxicity for cortical neuronal cells. Results are shown in Table 3 below.

Combinations of the invention strongly protect neurons from glutamate toxicity under experimental conditions described above. It is noteworthy that an effective protection is noticed using drug concentrations at which drugs, when used alone, have no significant or lower protective effect.

TABLE 3

| Drug Combination | Neuroprotective effect against glutamate toxicity |
|---|---|
| 3-phenylsulfonyl-8-(piperazin-1-yl) quinolone and baclofen | + |
| 3-phenylsulfonyl-8-(piperazin-1-yl) quinolone and acamprosate | + |
| 3-phenylsulfonyl-8-(piperazin-1-yl) quinolone and baclofen and acamprosate | + |
| 3-phenylsulfonyl-8-(piperazin-1-yl) quinolone and baclofen and donepezil | + |
| 3-phenylsulfonyl-8-(piperazin-1-yl) quinolone and acamprosate and donepezil | + |
| 3-phenylsulfonyl-8-(piperazin-1-yl) quinolone and baclofen and acamprosate and donepezil | + |
| 3-phenylsulfonyl-8-(piperazin-1-yl) quinolone and baclofen and memantine | + |
| 3-phenylsulfonyl-8-(piperazin-1-yl) quinolone and acamprosate and memantine | + |
| 3-phenylsulfonyl-8-(piperazin-1-yl) quinolone and baclofen and acamprosate and memantine | + |
| 3-phenylsulfonyl-8-(piperazin-1-yl) quinolone and baclofen and acamprosate and tacrine | + |
| 3-phenylsulfonyl-8-(piperazin-1-yl) quinolone and baclofen and acamprosate and rivastigmine | + |
| 3-phenylsulfonyl-8-(piperazin-1-yl) quinolone and baclofen and acamprosate and galantamine | + |

C—Protective Effect Against Ischemia/Hypdxia Induced Neuronal Cell Death.

Ischemic stress shares common physiological and genomic features with Parkinson's disease (notably mitochondrial dysfunction and oxidative stress).

Rat Neuronal Cortical Cells Preparation

Cells are prepared as previously.

Oxygen and Glucose Deprivation Assays (In Vitro Model of Ischemia)

The neuroprotective effect of compounds or combinations thereof is assessed by quantification of the neurite network (Neurofilament immunostaining (NF)) using MAP2 antibody. Riluzole, a neuroprotective drug, (Riluteck®, 5 μM) is used as positive control.

After 10 days of neuron culture, candidate drugs are solved in culture medium (+0.1% DMSO) and then pre-incubated with neurons for 1 hour before the oxygen and glucose deprivation. One hour after candidate drug (or combination) incubation, the medium is removed and fresh medium without glucose is added. This medium is composed by DMEM without glucose (Invitrogen) supplemented with 2% B27, 0.2 mM L-glutamine, 1% PS solution, 10 ng/ml of BDNF. The cells are transferred into an anaerobic incubator with 95% N2 and 5% $CO_2$ at 37° C.

After 2 hours, 25 mM of D-Glucose is added in culture medium and cells are transferred in classic incubator with 95% air/5% $CO_2$ at 37° C. After 24 hours of oxygen glucose reperfusion, cells are fixed by a cold solution of alcohol/acetic acid during 5 minutes.

After permeabilization with saponin (Sigma), cells are blocked for 2 hours with PBS containing 10% goat serum, then the cells are incubated with mouse monoclonal primary antibody against MAP2 (MAP2, Sigma). These antibodies are revealed with Alexa Fluor 488 goat anti-mouse IgG (Molecular probe).

Nuclei of cells are labelled by a fluorescent marker (Hoechst solution, SIGMA). Six wells per condition are used to assess neuronal survival in 3 different cultures.

Six wells per condition are used to assess neuronal survival in 3 different cultures. For each condition 2×10 pictures per well are taken and analyzed using InCell Analyzer™ 1000 (GE Healthcare) with 20× magnification.

Results

As shown in Table 4 below, all of the claimed drug combinations give a protective effect against ischemia/hypoxia induced cell death for cortical neuronal cells.

TABLE 4

| Drug Combination | Neuroprotection against Ischemia/Hypoxia induced cell death |
| --- | --- |
| 3-phenylsulfonyl-8-(piperazin-1-yl) quinolone and baclofen | + |
| 3-phenylsulfonyl-8-(piperazin-1-yl) quinolone and acamprosate | + |
| 3-phenylsulfonyl-8-(piperazin-1-yl) quinolone and baclofen and acamprosate | + |
| 3-phenylsulfonyl-8-(piperazin-1-yl) quinolone and baclofen and donepezil | + |
| 3-phenylsulfonyl-8-(piperazin-1-yl) quinolone and acamprosate and donepezil | + |
| 3-phenylsulfonyl-8-(piperazin-1-yl) quinolone and baclofen and acamprosate and donepezil | + |
| 3-phenylsulfonyl-8-(piperazin-1-yl) quinolone and baclofen and memantine | + |
| 3-phenylsulfonyl-8-(piperazin-1-yl) quinolone and acamprosate and memantine | + |
| 3-phenylsulfonyl-8-(piperazin-1-yl) quinolone and baclofen and acamprosate and memantine | + |
| 3-phenylsulfonyl-8-(piperazin-1-yl) quinolone and baclofen and acamprosate and tacrine | + |
| 3-phenylsulfonyl-8-(piperazin-1-yl) quinolone and baclofen and acamprosate and rivastigmine | + |
| 3-phenylsulfonyl-8-(piperazin-1-yl) quinolone and baclofen and acamprosate and galantamine | + |

Moreover, an effective protection is observed using drug concentrations at which drugs, alone, have no significant protective effect, thereby signing a potent and synergistic effect of the combination therapies on oxidative stress and mitochondrial dysfunction or apoptosis.

D—Neuro-Protective Effect of Drugs Against 6-OHDA-Injury on Dopaminergic Neurons 6-hydroxydopamine (6-OHDA) is a neurotoxic drug which selectively destroys dopaminergic neurons by generating reactive oxygen species and inducing mitochondrial death in the cells. Because of this nervous cell specificity, 6-OHDA toxicity is commonly used in vitro and in vivo to study Parkinsonism. Notwithstanding, a protective activity against oxidative stress and energy deprivation induced by 6-OHDA does show that combinations of the invention are efficient in protecting nervous cells from oxidative stress and energy deprivation that occur in other neurological disorders as multiple sclerosis, Alzheimer's Disease, frontotemporal dementia, amyotrophic lateral sclerosis, Parkinson's Disease, Huntington's Disease, neuropathies, alcoholism or alcohol withdrawal, or spinal cord injury.

Culture of Mesencephalic Dopaminergic Neurons

Rat dopaminergic neurons are cultured as described by Schinelli et al. [53]. Pregnant female rats of 15 days gestation are killed by cervical dislocation (Rats Wistar; Janvier) and the foetuses removed from the uterus. The embryonic midbrains are removed and placed in ice-cold medium of Leibovitz (L15; PanBiotech) containing 2% of Penicillin-Streptomycin (PS; PanBiotech) and 1% of bovine serum albumin (BSA; PanBiotech). Only the ventral portions of the mesencephalic flexure are used for the cell preparations as this is the region of the developing brain rich in dopaminergic neurons. The midbrains are dissociated by trypsinisation for 20 mM at 37° C. (Trypsin EDTA 1×; PanBiotech). The reaction is stopped by the addition of Dulbecco's modified Eagle's medium (DMEM; PanBiotech) containing DNAase I grade II (0.1 mg/ml; PanBiotech) and 10% of foetal calf serum (FCS; Invitrogen). Cells are then mechanically dissociated by 3 passages through a 10 ml pipette and centrifuged at 180×g for 10 mM at +4° c. on a layer of BSA (3.5%) in L15 medium. The supernatant is discarded and the cells of pellet are re-suspended in a defined culture medium consisting of Neurobasal (Invitrogen) supplemented with B27 (2%; Invitrogen), L-glutamine (2 mM; PanBiotech) and 2% of PS solution and 10 ng/ml of Brain-derived neurotrophic factor (BDNF, PanBiotech) and 1 ng/ml of Glial-Derived Neurotrophic Factor (GDNF, PanBiotech). Viable cells are counted in a Neubauer cytometer using the trypan blue exclusion test. The cells are seeded at a density of 40 000 cells/well in 96 well-plates (pre-coated with poly-L-lysine (Greiner)) and are cultured at 37° C. in a humidified air (95%)/CO2 (5%) atmosphere. Half of the medium is changed every 2 days with fresh medium. Five to six percents of the neuronal cell population are dopaminergic neurons.

6-OHDA and Tests Compounds Exposure

On day 6 of culture, the medium is removed and fresh medium is added, without or with 6-OHDA at the following concentrations: 20 μM during 48 hours diluted in control medium. Test compounds are pre-incubated for 1 h before the 6-OHDA application during 48 hours.

End Point Evaluation: Measure of Total Number of TH Positive Neurons

After 48 hours of intoxication with 6-OHDA, cells are fixed by a solution of 4% paraformaldehyde (Sigma) in PBS, pH=7.3 for 20 min at room temperature. The cells are washed again twice in PBS, and then permeabilized and non-specific sites are blocked with a solution of PBS containing 0.1% of saponin (Sigma) and 1% FCS for 15 min at room temperature. Then, cells are incubated with Monoclonal Anti-Tyrosine Hydroxylase antibody produced in mouse (TH, Sigma) at dilution of 1/1000 in PBS containing 1% FCS, 0.1% saponin, for 2 h at room temperature. These antibodies are revealed with Alexa Fluor 488 goat anti-mouse IgG (Molecular Probes) at the dilution 1/800 in PBS containing 1% FCS, 0.1% saponin, for 1 h at room temperature.

For each condition, 2×10 pictures (representing ~80% of total well area) per well are taken using InCell Analyzer™ 1000 (GE Healthcare) with 10× magnification. All images are taken in the same conditions. Analysis of the number of TH positive neurons are done using Developer software (GE Healthcare).

Data are expressed in percentage of control conditions (no intoxication, no 6OHDA=100%) in order to express the 6OHDA injury. All values are expressed as mean+/−SEM (s.e.mean) of the 3 cultures (n=6 wells per condition per culture). Statistical analyses consist in an ANOVA followed by the Dunnett's and PLSD Fisher's tests when it is allowed using Statview software version 5.0.

Results

A neuroprotective effect is observed for combinations of the invention in TH neurons survival test after 48 h 6-OHDA injury on dopaminergic neurons.

As shown in Table 5 below, all of the claimed drug combinations have a protective effect against 6-OHDA injury in dopaminergic neuronal cells.

TABLE 5

| Drug Combination | Protective effect against 6OHDA induced stereotaxic akinesia |
|---|---|
| 3-phenylsulfonyl-8-(piperazin-1-yl) quinolone and baclofen | + |
| 3-phenylsulfonyl-8-(piperazin-1-yl) quinolone and acamprosate | + |
| 3-phenylsulfonyl-8-(piperazin-1-yl) quinolone and baclofen and acamprosate | + |
| 3-phenylsulfonyl-8-(piperazin-1-yl) quinolone and baclofen and donepezil | + |
| 3-phenylsulfonyl-8-(piperazin-1-yl) quinolone and acamprosate and donepezil | + |
| 3-phenylsulfonyl-8-(piperazin-1-yl) quinolone and baclofen and acamprosate and donepezil | + |
| 3-phenylsulfonyl-8-(piperazin-1-yl) quinolone and baclofen and memantine | + |
| 3-phenylsulfonyl-8-(piperazin-1-yl) quinolone and acamprosate and memantine | + |
| 3-phenylsulfonyl-8-(piperazin-1-yl) quinolone and baclofen and acamprosate and memantine | + |
| 3-phenylsulfonyl-8-(piperazin-1-yl) quinolone and baclofen and acamprosate and tacrine | + |
| 3-phenylsulfonyl-8-(piperazin-1-yl) quinolone and baclofen and acamprosate and rivastigmine | + |
| 3-phenylsulfonyl-8-(piperazin-1-yl) quinolone and baclofen and acamprosate and galantamine | + |

Combinations of Table 5 show an effective protective effect against 6-OHDA injury in dopaminergic neuronal cells in comparison to the protective effect of the drug when used alone 3-phenylsulfonyl-8-(piperazin-1-yl) quinoline, baclofen, acamprosate, donepezil, memantine, tacrine, rivastigmine, galantamine.

E— Combination Therapies of the Invention Prevent Cognitive Impairment Induced by $A\beta_{25\text{-}42}$ Toxicity In Vivo The peptide amyloid-$\beta_{25\text{-}35}$ ($A\beta_{25\text{-}35}$) is the hydrophobic part of the full-length amyloid peptide. Injection of this peptide in the brain ventricles of rodents is known to induce a progressive neurodegenerative processes resulting in cognitive impairments. This model is commonly used for diseases involving cognitive impairment symptoms. The results showed that a combination of 3-phenylsulfonyl-8-(piperazin-1-yl) quinoline, baclofen and acamprosate were not only efficient but had a synergistic effect in protecting treated animals from the neurodegenerative processes due to the injection of toxic peptides.

Treatment Protocol

Male Swiss mice were administered from Day 0 to Day 10 with sham product (group 1 and 2); 3-phenylsulfonyl-8-(piperazin-1-yl) quinoline (group 3); baclofen and acamprosate (group 4); or 3-phenylsulfonyl-8-(piperazin-1-yl) quinoline, baclofen and acamprosate (group 5).

3-phenylsulfonyl-8-(piperazin-1-yl) quinoline) was administered orally by gavage once a day (1 mg/Kg of the individual body weight of each mouse).

A composition of baclofen and acamprosate was administered orally by gavage twice a day (respectively 480 μg/Kg and 32 μg/Kg of the individual body weight of each mouse).

At Day 1, oligomeric $A\beta_{25\text{-}35}$ peptide was injected ICV (intracerebroventricular) to provoke amyloid toxicity (group 2, 3, 4 and 5). Sc.Aβ peptide was injected ICV as negative control of oligomeric $A\beta_{25\text{-}35}$ peptide ICV injections (group 1). Male Swiss mice were anesthetized with isoflurane 2.5% and were injected ICV with $A\beta_{25\text{-}35}$ peptide (9 nmol/mouse) or Sc.Aβ peptide (9 nmol/mouse), in a final volume of 3 μl/mouse, according to the previously described method (Maurice et al., 1996, 1998; Meunier et al., 2006, 2013; Villard et al., 2009, 2011). Homogeneous oligomeric preparation of the $A\beta_{25\text{-}35}$ peptide was performed according to the AMYLGEN's owned procedure.

At Days 8-10, two different behavioral tests were performed to monitor the effects of the test compounds: the spontaneous alternation procedure in the Y-maze (assessing spatial working memory) at Day 8, and the step-through passive avoidance test at Day 9 (training session) and D 10 (retention session).

On Day 10, after the behavioral test, animals were euthanized.

Behavioral Analyses—Spontaneous Alternation Performance

Animals were tested for spontaneous alternation performance in the Y-maze, an index of spatial working memory. The Y-maze is made of grey polyvinylchloride. Each arm is 40 cm long, 13 cm high, 3 cm wide at the bottom, 10 cm wide at the top, and converging at an equal angle. Each mouse was placed at the end of one arm and allowed to move freely through the maze during an 8 min session. The series of arm entries, including possible returns into the same arm, was checked visually. An alternation was defined as entries into all three arms on consecutive occasions. The number of maximum alternations was therefore the total number of arm entries minus two and the percentage of alternation was calculated as (actual alternations/maximum alternations)× 100. Parameters included the percentage of alternation (memory index) and total number of arm entries (exploration index).

Animals that would show an extreme behavior (Alternation percentage<20% or >90% or number of arm entries<8) were discarded. Usually, it would account for 0-5% of the animals.

Behavioral Analyses—Passive Avoidance Test

All animals were tested for passive avoidance performance, an index of contextual long-term memory. The apparatus was a two-compartment (15×20×15 cm high) box with one illuminated with white polyvinylchloride walls and the other darkened with black polyvinylchloride walls and a grid floor. A guillotine door separated each compartment. A 60 W lamp positioned 40 cm above the apparatus lighted up the white compartment during the experiment. Scrambled footshocks (0.3 mA for 3 s) could be delivered to the grid floor using a shock generator scrambler (MedAssociates, USA). The guillotine door was initially closed during the training session. Each mouse was placed into the white compartment. After 5 s, the door was raised. When the mouse entered the darkened compartment and placed all its paws on the grid floor, the door was closed and the footshock delivered for 3 s. The step-through latency, that is, the latency spent to enter the darkened compartment, and the number of vocalizations were recorded. The retention test was carried out 24 h after training. Each mouse was placed again into the white compartment. After 5 s, the door was raised. The step-through latency was recorded up to 300 s.

Results

The combined studies showed that the association of 3-phenylsulfonyl-8-(piperazin-1-yl) quinoline, and baclofen and acamprosate, which at individual low doses, 3-phenylsulfonyl-8-(piperazin-1-yl) quinoline alone or baclofen and acamprosate alone, did not show any significant effect on the impairment of cognitive function, was able to reverse significantly the impairments induced by Aβ(25-35) in mice. The effect was significantly synergistic (Loewe's test) in both behavioral test (Y-maze CI=0.691 STPA CI=0.996).

REFERENCES

1 Crook R, Verkkoniemi A, Perez-Tur J, Mehta N, Baker M, Houlden H, Farrer M, Hutton M, Lincoln S, Hardy J, 1. Gwinn K, Somer M, Paetau A, Kalimo H, Ylikoski R, Poyhonen M, Kucera S & Haltia M (1998) A variant of Alzheimer's disease with spastic paraparesis and unusual plaques due to deletion of exon 9 of presenilin 1 *Nat. Med.* 4, 452-5.
2. Houlden H, Baker M, McGowan E, Lewis P, Hutton M, Crook R, Wood N W, Kumar-Singh S, Geddes J, Swash M, Scaravilli F, Holton J L, Lashley T, Tomita T, Hashimoto T, Verkkoniemi A, Kalimo H, Somer M, Paetau A, Martin J J, Van Broeckhoven C, Golde T, Hardy J, Haltia M & Revesz T (2000) Variant Alzheimer's disease with spastic paraparesis and cotton wool plaques is caused by PS-1 mutations that lead to exceptionally high amyloid-beta concentrations. *Ann. Neurol.* 48, 806-8.
3. Kwok J B, Taddei K, Hallupp M, Fisher C, Brooks W S, Broe G A, Hardy J, Fulham M J, Nicholson G A, Stell R, St George Hyslop P H, Fraser P E, Kakulas B, Clarnette R, Relkin N, Gandy S E, Schofield P R & Martins R N (1997) Two novel (M233T and R278T) presenilin-1 mutations in early-onset Alzheimer's disease pedigrees and preliminary evidence for association of presenilin-1 mutations with a novel phenotype. *Neuroreport* 8, 1537-42.
4. Verkkoniemi A, Kalimo H, Paetau A, Somer M, Iwatsubo T, Hardy J & Haltia M (2001) Variant Alzheimer disease with spastic paraparesis: neuropathological phenotype. *J. Neuropathol. Exp. Neurol.* 60, 483-92.
5. Citron M (2004) Strategies for disease modification in Alzheimer's disease. *Nat. Rev. Neurosci.* 5, 677-85.
6. Suh Y-H & Checler F (2002) Amyloid precursor protein, presenilins, and alpha-synuclein: molecular pathogenesis and pharmacological applications in Alzheimer's disease. *Pharmacol. Rev.* 54, 469-525.
7. Blacker D, Albert M S, Bassett S S, Go R C, Harrell L E & Folstein M F (1994) Reliability and validity of NINCDS-ADRDA criteria for Alzheimer's disease. The National Institute of Mental Health Genetics Initiative. *Arch. Neurol.* 51, 1198-204.
8. Rossor M N, Fox N C, Freeborough P A & Harvey R J (1996) Clinical features of sporadic and familial Alzheimer's disease. *Neurodegeneration* 5, 393-7.
9. Glenner G G, Wong C W, Quaranta V & Eanes E D (1984) The amyloid deposits in Alzheimer's disease: their nature and pathogenesis. *Appl. Pathol.* 2, 357-69.
10. Ballatore C, Lee V M-Y & Trojanowski J Q (2007) Tau-mediated neurodegeneration in Alzheimer's disease and related disorders. *Nat. Rev. Neurosci.* 8, 663-72.
11. DiLuca M, Bell K F S & Claudio Cuello A (2006) Altered synaptic function in Alzheimer's disease. *Eur. J. Pharmacol.* 545, 11-21.
12. Hardy J A & Higgins G A (1992) Alzheimer's disease: the amyloid cascade hypothesis. *Science* 256, 184-5.
13. Braak H & Braak E (1991) Neuropathological stageing of Alzheimer-related changes. *Acta Neuropathol.* 82, 239-59.
14. Golde T E (2005) The Abeta hypothesis: leading us to rationally-designed therapeutic strategies for the treatment or prevention of Alzheimer disease. *Brain Pathol.* 15, 84-7.
15. Hardy J & Selkoe D J (2002) The amyloid hypothesis of Alzheimer's disease: progress and problems on the road to therapeutics. *Science* 297, 353-6.
16. Selkoe D J (2000) The genetics and molecular pathology of Alzheimer's disease: roles of amyloid and the presenilins. *Neurol. Clin.* 18, 903-22.
17. Zlokovic B V (2008) The blood-brain barrier in health and chronic neurodegenerative disorders. *Neuron* 57, 178-201.
18. Budd Haeberlein S L & Lipton S A (2009) Excitotoxicity in neurodegenerative disease. In *Encyclopedia of neuroscience* (Squire L R, ed), pp. 77-86. Elsevier.
19. Mosconi L, Pupi A & De Leon M J (2008) Brain glucose hypometabolism and oxidative stress in preclinical Alzheimer's disease. *Ann. N. Y. Acad. Sci.* 1147, 180-95.
20. Struble R G, Ala T, Patrylo P R, Brewer G J & Yan X-X (2010) Is brain amyloid production a cause or a result of dementia of the Alzheimer's type? *J. Alzheimers. Dis.* 22, 393-9.
21. Cunnane S, Nugent S, Roy M, Courchesne-Loyer A, Croteau E, Tremblay S, Castellano A, Pifferi F, Bocti C, Paquet N, Begdouri H, Bentourkia M, Turcotte E, Allard M, Barberger-Gateau P, Fulop T & Rapoport S I (2011) Brain fuel metabolism, aging, and Alzheimer's disease. *Nutrition* 27, 3-20.
22. Uemura E & Greenlee H W (2001) Amyloid beta-peptide inhibits neuronal glucose uptake by preventing exocytosis. *Exp. Neurol.* 170, 270-6.
23. McGleenon B M, Dynan K B & Passmore A P (1999) Acetylcholinesterase inhibitors in Alzheimer's disease. *Br. J. Clin. Pharmacol.* 48, 471-480.
24. Parsons C G, Danysz W & Quack G (1999) Memantine is a clinically well tolerated N-methyl-D-aspartate (NMDA) receptor antagonist—a review of preclinical data. *Neuropharmacology* 38, 735-67.
25. Gauthier S & Scheltens P (2009) Can we do better in developing new drugs for Alzheimer's disease? *Alzheimer's Dement.* 5, 489-491.
26. Aliabadi A, Foroumadi A, Mohammadi-Farani A & Garmsiri Mahvar M (2013) Synthesis and Evaluation of Anti-acetylcholinesterase Activity of 2-(2-(4-(2-Oxo-2-phenylethyl)piperazin-1-yl) ethyl)Isoindoline-1,3-dione Derivatives with Potential Anti-Alzheimer Effects. *Iran. J. Basic Med. Sci.* 16, 1049-54.
27. Kaduszkiewicz H & Hoffmann F (2008) Review: cholinesterase inhibitors and memantine consistently but marginally improve symptoms of dementia. *Evid. Based. Ment. Health* 11, 113.
28. Galvin J E (2012) OPTIMIZING DIAGNOSIS AND MANANGEMENT IN MILD-TO-MODERATE ALZHEIMER'S DISEASE. *Neurodegener. Dis. Manag.* 2, 291-304.
29. Lipton S A (2004) Failures and successes of NMDA receptor antagonists: molecular basis for the use of open-channel blockers like memantine in the treatment of acute and chronic neurologic insults. *NeuroRx* 1, 101-10.
30. Lipton S A (2006) Paradigm shift in neuroprotection by NMDA receptor blockade: memantine and beyond. *Nat. Rev. Drug Discov.* 5, 160-70.
31. Stella V J (2007) *Prodrugs: challenges and rewards.* (A. Press and Springer, eds.) Springer Singapore Pte. Limited, New-York.
32. Wermuth C G (2011) *The Practice of Medicinal Chemistry* Elsevier Science.
33. Pezron I, Mitra A K, Duvvuri S & Tirucherai G S (2002) Prodrug strategies in nasal drug delivery. *Expert Opin. Ther. Pat.* 12, 331-340.
34. Stella V J (2004) Prodrugs as therapeutics. *Expert Opin. Ther. Pat.* 14, 277-280.
35. Stella V J & Nti-Addae K W (2007) Prodrug strategies to overcome poor water solubility. *Adv. Drug Deliv. Rev.* 59, 677-94.

36 Beaumont K, Webster R, Gardner I & Dack K (2003) Design of ester prodrugs to enhance oral absorption of poorly permeable compounds: challenges to the discovery scientist. *Curr. Drug Metab.* 4, 461-85.

37 Higuchi T & Stella V J (1975) *Pro-drugs as Novel Drug Delivery System*, ACS Sympos American Chemical Society, Washington, D.C.

38 Roche E B (1977) *Design of biopharmaceutical properties through prodrugs and analogs: a symposium*, American P The Academy, Washington, D.C.

39 Lal R, Sukbuntherng J, Tai E H L, Upadhyay S, Yao F, Warren M S, Luo W, Bu L, Nguyen S, Zamora J, Peng G, Dias T, Bao Y, Ludwikow M, Phan T, Scheuerman R A, Yan H, Gao M, Wu Q Q, Annamalai T, Raillard S P, Koller K, Gallop M A & Cundy K C (2009) Arbaclofen placarbil, a novel R-baclofen prodrug: improved absorption, distribution, metabolism, and elimination properties compared with R-baclofen. *J. Pharmacol. Exp. Ther.* 330, 911-21.

40 Xu F, Peng G, Phan T, Dilip U, Chen J L, Chernov-Rogan T, Zhang X, Grindstaff K, Annamalai T, Koller K, Gallop M A & Wustrow D J (2011) Discovery of a novel potent GABA(B) receptor agonist. *Bioorg. Med. Chem. Lett.* 21, 6582-5.

41 Wishart D S, Knox C, Guo A C, Cheng D, Shrivastava S, Tzur D, Gautam B & Hassanali M (2008) DrugBank: a knowledgebase for drugs, drug actions and drug targets. *Nucleic Acids Res.* 36, D901-6.

42 Leach A R & Gillet V J *An Introduction to Chemoinformatics* (Springer-Verlag New York Inc, ed.).

43 Rahman S A, Bashton M, Holliday G L, Schrader R & Thornton J M (2009) Small Molecule Subgraph Detector (SMSD) toolkit. *J. Cheminform.* 1, 12.

44 Stahl H & Wermuth C G (2011) *Pharmaceutical salts: Properties, selection, and use,* 2nd ed. (Wiley-VCH, ed.).

45 Hanafi R, Mosad S, Abouzid K, Niess R & Spahn-Langguth H (2011) Baclofen ester and carbamate prodrug candidates: a simultaneous chromatographic assay, resolution optimized with DryLab. *J. Pharm. Biomed. Anal.* 56, 569-76.

46 Chou T-C (2006) Theoretical basis, experimental design, and computerized simulation of synergism and antagonism in drug combination studies. *Pharmacol. Rev.* 58, 621-81.

47 Grabovsky Y & Tallarida R J (2004) Isobolographic analysis for combinations of a full and partial agonist: curved isoboles. *J. Pharmacol. Exp. Ther.* 310, 981-6.

48 Berenbaum M C (1977) Synergy, additivism and antagonism in immunosuppression. A critical review. *Clin. Exp. Immunol.* 28, 1-18.

49 Slinker B K (1998) The statistics of synergism. *J. Mol. Cell. Cardiol.* 30, 723-31.

50 Gennaro A R (2000) Remington: The Science and Practice of Pharmacy, 20th ed. (A. D. Gennaro, W. Lippincott, and Wilkins, eds.) Lippincott Williams & Wilkins.

51 Swarbrick J & Boylan J C (eds.) *Encyclopedia of Pharmaceutical Technology* Dekker, Marcel, New-York.

52 Singer C A, Figueroa-Masot X A, Batchelor R H & Dorsa D M (1999) The mitogen-activated protein kinase pathway mediates estrogen neuroprotection after glutamate toxicity in primary cortical neurons. *J. Neurosci.* 19, 2455-63.

53 Schinelli S, Zuddas A, Kopin I J, Barker J L & di Porzio U (1988) 1-Methyl-4-phenyl-1,2,3,6-tetrahydropyridine metabolism and 1-methyl-4-phenylpyridinium uptake in dissociated cell cultures from the embryonic mesencephalon. *J. Neurochem.* 50, 1900-7.

The invention claimed is:

1. A method of treatment of a neurological disorder in a subject in need thereof, comprising administering to the subject a combination of compounds comprising (i) 3-phenylsulfonyl-8-(piperazin-1-yl) quinoline or a salt, derivative or prodrug thereof and (ii) baclofen and acamprosate, or salts, derivatives or prodrugs thereof, wherein the neurological disorder is selected from Alzheimer's disease (AD), an AD related disorder, Parkinson's disease, Lewy body dementia, multiple system atrophy and other related synucleinopathies, Huntington's disease, amyotrophic lateral sclerosis, multiple sclerosis, peripheral neuropathies, alcoholism or alcohol withdrawal, neurological manifestations of drug abuse or drug abuse withdrawal, spinal cord injury, epilepsy, traumatic brain injury or a brain ischemic event.

2. The method according to claim 1, wherein the neurological disorder is selected from Alzheimer's disease (AD) or an AD related disorder.

3. The method according to claim 1, further comprising administering at least one drug selected from the group consisting of donepezil, memantine, rivastigmine, tacrine and galantamine, or salts, derivatives or prodrugs thereof.

4. The method according to claim 3, comprising administering one of the following combinations of compounds:
 3-phenylsulfonyl-8-(piperazin-1-yl) quinoline and baclofen and acamprosate and donepezil,
 3-phenylsulfonyl-8-(piperazin-1-yl) quinoline and baclofen and acamprosate and memantine,
 3-phenylsulfonyl-8-(piperazin-1-yl) quinoline and baclofen and acamprosate and tacrine,
 3-phenylsulfonyl-8-(piperazin-1-yl) quinoline and baclofen and acamprosate and rivastigmine, or
 3-phenylsulfonyl-8-(piperazin-1-yl) quinoline and baclofen and acamprosate and galantamine, or salts, derivatives or prodrugs thereof.

5. The method according to claim 1, wherein the neurological disorder is selected from Parkinson's disease, Lewy body dementia, multiple system atrophy and other related synucleinopathies.

6. The method according to claim 1, wherein the neurological disorder is Parkinson's disease.

7. The method according to claim 6, further comprising administering levodopa.

8. The method according to claim 1, wherein the compounds are administered separately, simultaneously or sequentially.

9. The method according to claim 1, wherein the compounds are formulated and administered together.

10. The method according to claim 1, wherein acamprosate is a calcium salt of acamprosate.

11. A pharmaceutical composition comprising (i) 3-phenylsulfonyl-8-(piperazin-1-yl) quinoline and (ii) baclofen and (iii) acamprosate, or salts, derivatives or prodrugs thereof.

12. The pharmaceutical composition according to claim 11, further comprising at least one compound selected from the group consisting of donepezil, memantine, rivastigmine, tacrine, galantamine and levodopa, or salts, derivatives or prodrugs thereof.

13. The pharmaceutical composition according to claim 12, comprising:
 3-phenylsulfonyl-8-(piperazin-1-yl) quinoline and baclofen and acamprosate and donepezil,
 3-phenylsulfonyl-8-(piperazin-1-yl) quinoline and baclofen and acamprosate and memantine,
 3-phenylsulfonyl-8-(piperazin-1-yl) quinoline and baclofen and acamprosate and tacrine, 3-phenylsulfonyl-8-(piperazin-1-yl) quinoline and baclofen and acamprosate and rivastigmine, or 3-phenylsulfonyl-8-(piperazin-1-yl) quinoline and baclofen and acamprosate and galantamine, or salts, derivatives or prodrugs thereof.

14. The pharmaceutical composition according to claim 12, comprising:

3-phenylsulfonyl-8-(piperazin-1-yl) quinoline and baclofen and acamprosate and levodopa, or salts, derivatives or prodrugs thereof.

15. The pharmaceutical composition according to claim 11 wherein acamprosate is a calcium salt of acamprosate.

16. A method for treating a neurological disorder in a subject, comprising administering to the subject a pharmaceutical composition comprising (i) 3-phenylsulfonyl-8-(piperazin-1-yl) quinoline or a salt, derivative or prodrug thereof and (ii) baclofen and (iii) acamprosate, or salts, derivatives or prodrugs thereof, wherein the neurological disorder is selected from the group consisting of Alzheimer's disease (AD), an AD related disorder, Parkinson's disease, Lewy body dementia, multiple system atrophy and other related synucleinopathies, Huntington's disease, amyotrophic lateral sclerosis, multiple sclerosis, peripheral neuropathies, alcoholism or alcohol withdrawal, neurological manifestations of drug abuse or drug abuse withdrawal, spinal cord injury, epilepsy, traumatic brain injury and a brain ischemic event.

17. The method according to claim 16, wherein the neurological disorder is treating Alzheimer's disease or an AD related disorder.

18. The method according to claim 16, wherein the neurological disorder is Parkinson's disease.

19. The method according to claim 16, wherein, when acamprosate is present, acamprosate is a calcium salt of acamprosate.

* * * * *